United States Patent
McCarthy et al.

(10) Patent No.: US 10,556,087 B2
(45) Date of Patent: Feb. 11, 2020

(54) ENHANCING MUSIC FOR REPETITIVE MOTION ACTIVITIES

(71) Applicant: MedRhythms, Inc., Portland, ME (US)

(72) Inventors: Owen McCarthy, Gorham, ME (US); Brian Harris, Gray, ME (US); Alex Kalpaxis, Glendale, NY (US); David Guerette, Gorham, ME (US)

(73) Assignee: MEDRHYTHMS, INC., Portland, OR (US)

( * ) Notice: Subject to any disclaimer, the term of this patent is extended or adjusted under 35 U.S.C. 154(b) by 0 days.

(21) Appl. No.: 16/044,240

(22) Filed: Jul. 24, 2018

(65) Prior Publication Data
US 2019/0022351 A1    Jan. 24, 2019

Related U.S. Application Data

(60) Provisional application No. 62/536,264, filed on Jul. 24, 2017.

(51) Int. Cl.
*A61M 21/02* (2006.01)
*A61M 21/00* (2006.01)

(52) U.S. Cl.
CPC ..... *A61M 21/02* (2013.01); *A61M 2021/0027* (2013.01); *A61M 2205/3375* (2013.01);
(Continued)

(58) Field of Classification Search
CPC .......... A61M 21/02; A61M 2210/0662; A61M 21/00; A61M 2205/3584; A61M 2205/52;
(Continued)

(56) References Cited

U.S. PATENT DOCUMENTS 6,656,137 B1 * 12/2003 Tyldsley ............... A61M 21/00
434/185
8,801,591 B1 * 8/2014 Lasorso, Jr. .......... A61H 1/005
600/28

(Continued)

FOREIGN PATENT DOCUMENTS

WO    WO-2017/031247 A1    2/2017

OTHER PUBLICATIONS

International Search Report and Written Opinion for International Application No. PCT/US2018/43525 dated Oct. 12, 2018.

*Primary Examiner* — Navin Natnithithadha
*Assistant Examiner* — Sunita Reddy
(74) *Attorney, Agent, or Firm* — Leason Ellis LLP

(57) ABSTRACT

A method of providing repetitive motion therapy comprising providing access to audio content; selecting audio content for delivery to a patient; performing an analysis on the selected audio content, the analysis identifying audio features of the selected audio content, and extracting rhythmic and structural features of the selected audio content; performing an entrainment suitability analysis on the selected audio content; generating entrainment assistance cue(s) to the selected audio content, the assistance cue(s) including a sound added to the audio content; applying the assistance cues to the audio content simultaneously with playing the selected audio content; evaluating a therapeutic effect on the patient, wherein the selected audio content continues to play when a therapeutic threshold is detected, and a second audio content is selected for delivery to the patient when a therapeutic threshold is not detected.

20 Claims, 35 Drawing Sheets

(52) U.S. Cl.
CPC . *A61M 2205/3584* (2013.01); *A61M 2205/52* (2013.01); *A61M 2210/0662* (2013.01); *G10H 2210/076* (2013.01); *G10H 2210/391* (2013.01)

(58) Field of Classification Search
CPC .. A61M 2021/0027; A61M 2205/3375; G10H 2210/076; G10H 2210/391
USPC .................................................... 600/26–28
See application file for complete search history.

(56) References Cited

U.S. PATENT DOCUMENTS

| | | | | |
|---|---|---|---|---|
| 9,457,166 | B1 * | 10/2016 | Lasorso, Jr. | A61M 21/02 |
| 2006/0102171 | A1 * | 5/2006 | Gavish | A61B 5/0816 128/95.1 |
| 2007/0000374 | A1 * | 1/2007 | Clark | G10H 1/0008 84/724 |
| 2009/0221928 | A1 * | 9/2009 | Einav | A61B 5/0484 600/544 |
| 2010/0168503 | A1 * | 7/2010 | Sunnen | A61M 21/00 600/26 |
| 2011/0166488 | A1 * | 7/2011 | Miyake | A61B 5/112 601/34 |
| 2011/0184225 | A1 * | 7/2011 | Whitall | A63B 24/0003 600/28 |
| 2013/0131555 | A1 * | 5/2013 | Hook | A61B 5/112 600/595 |
| 2014/0256511 | A1 * | 9/2014 | Smith | G10H 7/00 482/8 |
| 2014/0366710 | A1 | 12/2014 | Eronen et al. | |
| 2015/0297109 | A1 * | 10/2015 | Garten | A61B 5/04845 600/544 |
| 2017/0080320 | A1 * | 3/2017 | Smith | G10H 1/42 |

* cited by examiner

ENHANCING MUSIC FOR REPETITIVE MOTION ACTIVITIES

CROSS REFERENCE TO RELATED APPLICATIONS

This application claims the benefit of priority under 35 USC 119(e) of Provisional application No. 62/536,264 filed Jul. 24, 2017, the entire contents of which are incorporated herein.

FIELD OF THE DISCLOSED SUBJECT MATTER

Music enhances a wide array of brain regions at one time. Physiological research has shown that auditory rhythm has a profound effect on the motor system. Evidence reveals that the auditory and motor systems have strong connectivity on cortical, sub-cortical and spinal levels. In practice, this phenomenon is referred to as entrainment. Knowing the richness of these connections, a large number of clinical studies have researched the effectiveness of rhythm and music to produce functional changes through neurological motor therapy for patients who suffer from brain injuries.

Since the formal development of this therapy, much research has been conducted to test its effectiveness clinically. One study was designed with stroke patients post cerebral vascular accident to understand the effect of Rhythmic Auditory Stimulation (RAS) on their gait patterns. After establishing a baseline walk of 6 meters, the following walking trials were matched with RAS. The results showed that an auditory-motor synchronization developed for most patients. Their stride symmetry and stride length under RAS improved significantly ($p<0.05$). Also in an Electromyogram (EMG) recording of the patients, there was improved muscle activation on the paretic side.

In another study, stroke patients underwent RAS therapy and stroke patients used conventional physical therapy for gait training. The results showed a significantly stronger improvement in gait velocity and stride length for RAS group. Their gait velocity improved by 165% while the control group improved by 107%. Also, Parkinson patients showed clear improvements in their bradykinesia symptoms after undergoing music therapy ($p<0.0001$). The effects of stimulating rhythmic music on the coordination of Parkinson's patients has been analyzed and after 3 weeks of this rhythmic music therapy, the patients demonstrated a longer stride length and improved gait velocity by an average of 25%.

Research in the rhythmic auditory facilitation of gait patterns of patients with Parkinson's disease shows consistent gait improvements. The research reveals that speeding up the rhythm in the music increased the gait velocity, cadence and stride length significantly. This further validates the effectiveness of auditory rhythm to improve gait through the rhythmic coupling of auditory and motor systems. There was a significant increased improvement for those patients undergoing music therapy versus the control patients, using an EEG comparison between groups reveals more cortical connectivity and further activation of the motor cortex in patients who undergo Neurologic Music Therapy (NMT).

It has also been shown that rhythm enhances the brain at a brain stem level through the existence of audio-motor pathways via reticulospinal connection. Auditory projections in the cerebellum have been shown via the pontine nuclei. In addition, the inferior colliculi, one of the ascending auditory pathways, project through the thalamus to the striatum of the basal ganglia. The basal ganglia maintain key projection to the cortical structures including the supplementary motor cortex and pre-motor cortex. Also, the auditory association areas projecting back to the basal ganglia influence the function of timing and sequencing selection. In Moore et al 2017, it was demonstrated that by providing music-cued motor-training it facilitates a thickening and change in a brain region called the arcuate fasciculus, which plays an important role in motor planning (Moore et al, 2017). These processes and pathways provides evidence behind the significant effects of auditory rhythm of music therapy on motor output.

Throughout history, music has been shown to be a universal language across cultures (Blacking, 1976) and have the capacity to convey emotional saliency to listeners regardless of verbal content. Emotionally salient information had been shown to elicit greatest behavioral change, even in severe traumatic brain injury. (Boly et al., 2004; Perrin et al., 2006; Machado et al., 2007). A recent study showed that live preferred music yielded the highest levels of cognitive responses in terms of arousal and awareness, in both healthy subjects and subjects in a vegetative state in comparison to other auditory input including improvised music, disliked music, white noise and silence (O'Kelly, et al., 2013).

What is needed in the art is a technique that uses music in a session in order improve some physical functionality, such as gait, gross motor skills, rhythmic speech, dexterity, respiration, etc., by inducing entrainment of the physical activity to a musical piece. A technique is provided which analyzes an audio file, such as a user's preferred music, extracts salient musical features, determines its suitability for use in a session, and, if necessary, enhances entrainment suitability factors such as rhythmic stability and beat strength to allow it to be used in a session.

"Rhythmic stability" is a composite score that factors variance across tempo, time signature/meter, and rhythmic patterns. "Beat strength" is the perceived loudness of sounds occurring at the beat (the rate at which a listener naturally taps along with the music) and is measured in root-mean-square (RMS) energy. The beat is often, but not necessarily, carried in a percussive instrument such as drums. These and other suitability factors are explored further in Section 2: Entrainment Suitability.

Recorded music typically contains dynamic aspects like changing tempo and time signatures, sections with a weak or nonexistent rhythmic pulse, fade-ins/outs, syncopation, etc, and rarely has homogenous, static features from start to finish. These are inherent parts of an expressive musical performance, but they also present a variety of challenges when used for entrainment. At its simplest, an effective RAS stimulus is a metronome playing a click at even beat intervals at a desired tempo; effective but lacking in interesting musical features a listener may associate with preferred music. Likewise, the ideal music selection for a repetitive motion activity also has constant, even beat intervals at a static tempo and strong beat strength, such as Michael Jackson's "Billie Jean" or Mark Ronson's "Uptown Funk". Poor entrainment songs ("song" defined as a piece of audio content with non-zero length) include those lacking discernible rhythm ("Under Stars" by Brian Eno) or those containing sudden tempo modulations ("Band on the Run" by Paul McCartney and Wings). Additionally, certain genres contain macro-trends that can be identified, which can provide classification data (e.g. hip hop is typically recorded to a drum machine which as a result provides less tempo variance). The techniques described herein are capable of manipulating the preferred music of users to improve its suitability for therapeutic sessions, even if it contains these complexities within an addressable range. For example, through assistive cues or enhancements to the audio signal, the rhythmic stability of the music is improved for use in therapeutic movement.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter includes a method of providing repetitive motion therapy comprising providing access to audio content; selecting audio content for delivery to a patient; performing an analysis on the selected audio content, the analysis identifying audio features of the selected audio content, and extracting rhythmic and structural features of the selected audio content; performing an entrainment suitability analysis on the selected audio content; generating entrainment assistance cue(s) to the selected audio content, the assistance cue(s) including a sound added to the audio content; applying the assistance cues to the audio content simultaneously with playing the selected audio content; evaluating a therapeutic effect on the patient, wherein the selected audio content continues to play when a therapeutic threshold is detected, and a second audio content is selected for delivery to the patient when a therapeutic threshold is not detected.

In some embodiments, the method further comprises updating the repository of audio content to integrate feedback from the evaluating step.

In some embodiments, performing an analysis on the selected audio content includes providing bounds to a beat tracking algorithm.

In some embodiments, the audio content includes music and the bounds are an average of tempo of the music genre.

In some embodiments, performing the analysis on the audio content includes applying an onset detection function (ODF), and correlating results of each ODF to beat times of the audio signal.

In some embodiments, the method further includes generating modification(s) to the selected audio content, with at least one modification including an adjustment to the timing of the audio content.

In some embodiments, the audio content is streamed to the patient.

In some embodiments, a method of providing repetitive motion therapy comprises: providing a repository of audio content; selecting audio content for delivery to a patient; performing an analysis on the selected audio content, the analysis identifying high and low level features of the selected audio content; the analysis determining a tempo of the selected audio content;
performing an entrainment analysis on the selected audio content, the entrainment analysis assigning a suitability score to a plurality of music aspects; generating entrainment assistance cue(s) to the selected audio content, the assistance cue(s) including a sound added to the selected audio content; applying the assistance cue(s) to the audio file simultaneously with playing the selected audio content; evaluating a therapeutic effect on the patient, wherein the selected audio content continues to play when a therapeutic threshold is detected, and a second audio content selection is selected for delivery to the patient when a therapeutic threshold is not detected; and updating the database of audio content to integrate feedback from the evaluating step.

In some embodiments, the entrainment analysis determines an entrainment suitability score for at least one of the following: average tempo, beat strength, beat times confidence, rhythmic stability, time signature, tempo perception confidence, or effective duration.

In some embodiments, generating entrainment assistance cue(s) includes a single beat musical cue which is played on each beat of the selected audio content.

In some embodiments, the musical cue is delivered to a single ear of the patient.

In some embodiments, the musical cue is added to sections of the audio content exhibiting low rhythmic stability.

In some embodiments, the method further comprises generating modification(s) to the selected audio content, with at least one modification including an adjustment to the timing of the audio content.

In some embodiments, generating modification(s) to the first audio content includes providing drum reinforcement to the audio content.

In some embodiments, generating modification(s) to the first audio content includes providing structural modification to the audio content.

In some embodiments, the method of providing repetitive motion therapy comprises: providing a repository of audio content; selecting audio content for delivery to a patient; performing an analysis on the selected audio content, the analysis identifying high and low level features of the audio content; the analysis determining a tempo of the audio content; performing an entrainment analysis on the audio content, the entrainment analysis assigning a suitability score to aspects including at least one of: average tempo; tempo variance; tempo perception; time signature; rhythmic pattern variance; detection of rhythmic parts at a plurality of sections throughout the audio content; and position of first and last beat in the audio content; generating entrainment assistance cue(s) to the audio content, the assistance cue(s) including a sound added to the audio content, the sound added including at least one of: a single percussive sound, played on a quarter note of the audio content; a percussive sound, played on a beat of the audio content and its subdivisions; a drum pattern synchronized with the audio content; and a voice counting beats of the audio content.

In some embodiments, the repetitive motion includes walking.

In some embodiments, the method further comprises assigning an entrainability score to the audio content based on the correlation of the patient cadence with the tempo of the audio content.

In some embodiments, an entrainability score is determined before and after application of an entrainment assistance cue(s) to the audio content.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the method and system of the disclosed subject matter. Together with the description, the drawings serve to explain the principles of the disclosed subject matter.

BRIEF DESCRIPTION OF THE DRAWINGS

A detailed description of various aspects, features, and embodiments of the subject matter described herein is provided with reference to the accompanying drawings, which are briefly described below. The drawings are illustrative and are not necessarily drawn to scale, with some components and features being exaggerated for clarity. The drawings illustrate various aspects and features of the present subject matter and may illustrate one or more embodiment(s) or example(s) of the present subject matter in whole or in part.

DETAILED DESCRIPTION OF AN EXEMPLARY EMBODIMENT

Reference will now be made in detail to exemplary embodiments of the disclosed subject matter, an example of which is illustrated in the accompanying drawings. The method and corresponding steps of the disclosed subject matter will be described in conjunction with the detailed description of the system.

Figure 1:
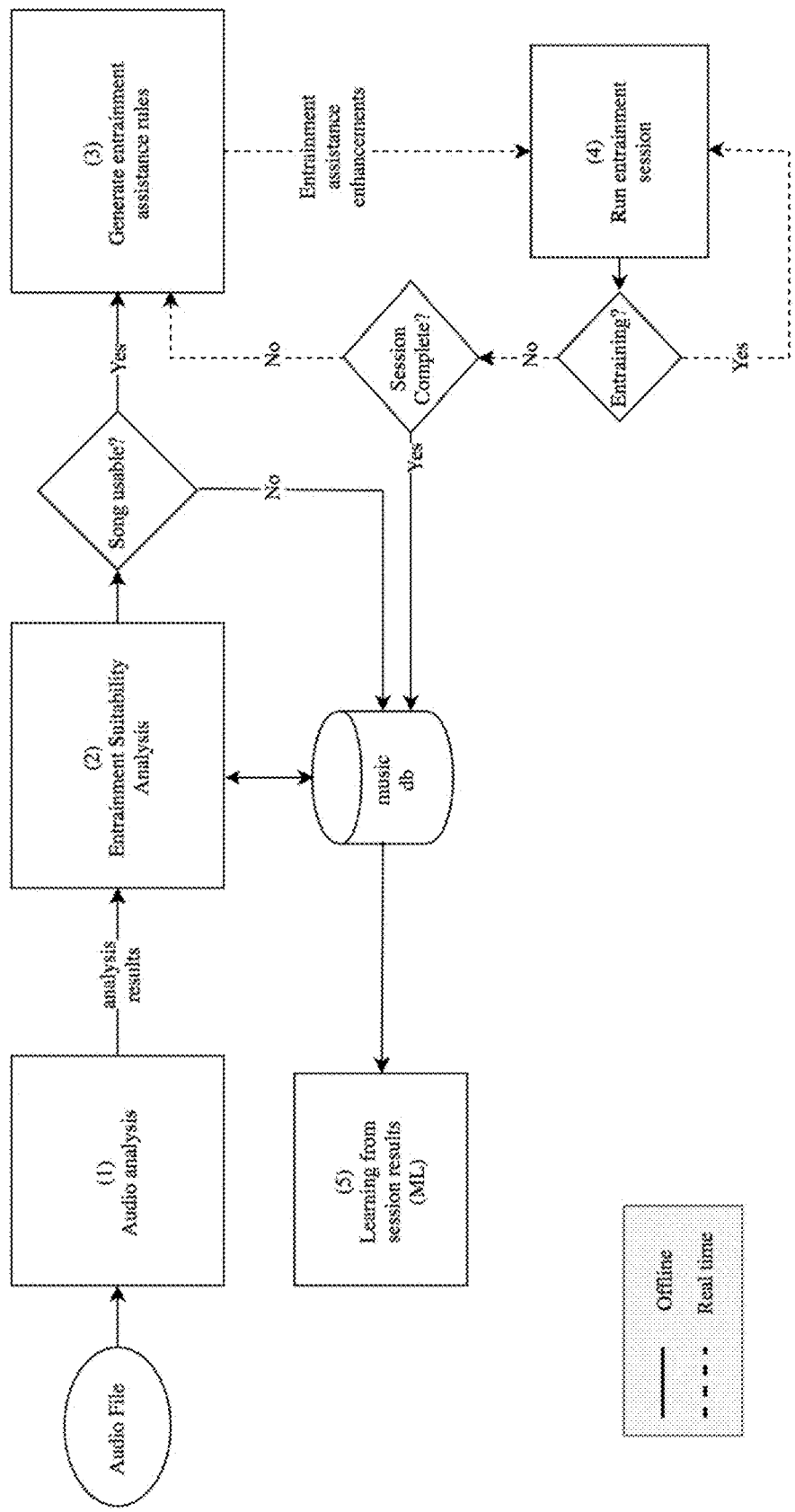
FIG. 1 is a flow chart of an exemplary embodiment of a computer-generated analysis in accordance with the present disclosure.
Figure 2:
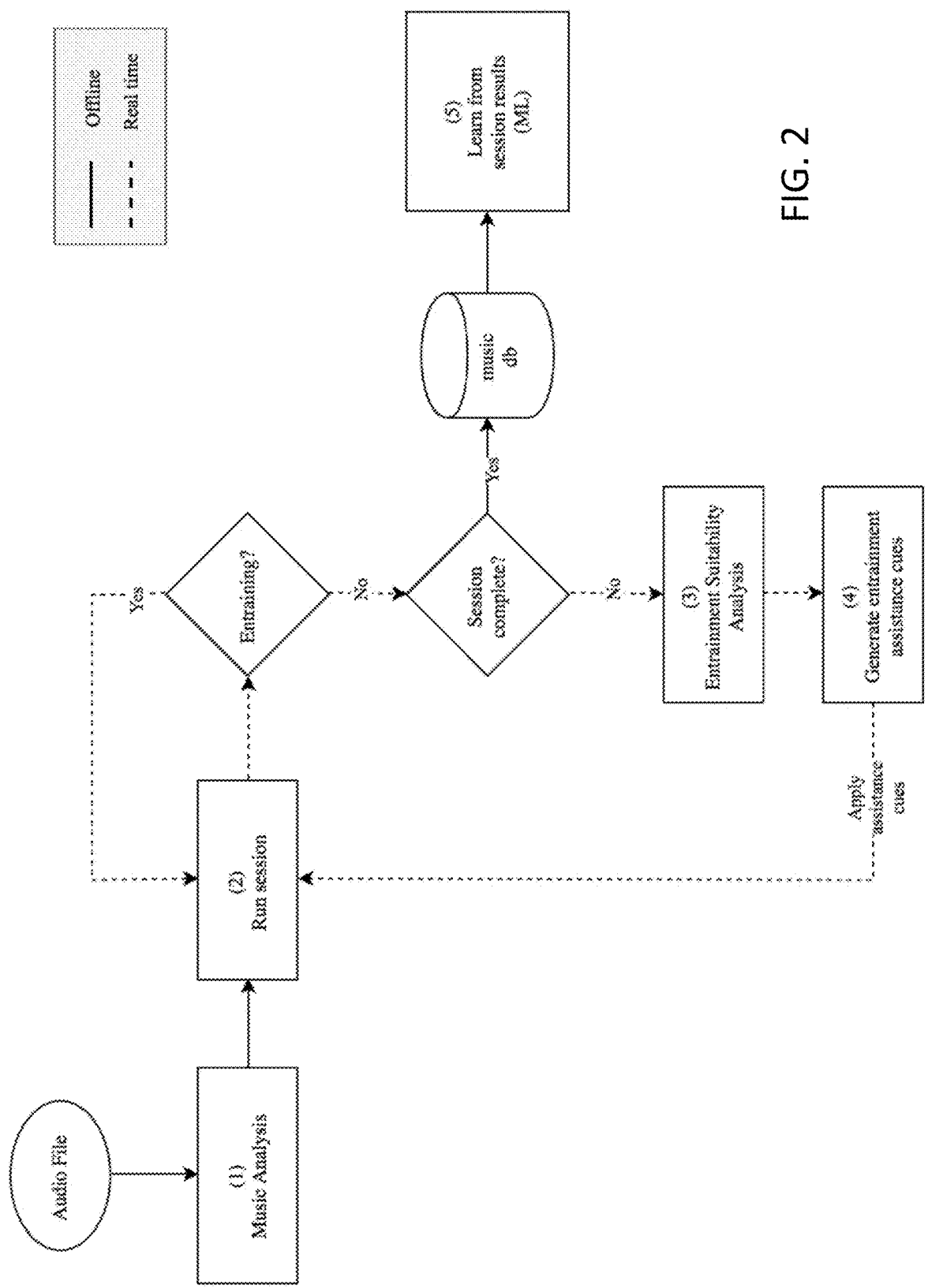
FIG. 2 is a flow chart of an exemplary embodiment of a user-verified analysis in accordance with the present disclosure.

The described process can follow two different steps as shown in FIG. 1 and FIG. 2, as well as a combination of the two processes. The first process is a "computer-generated analysis" and the second process is a "user-driven analysis."

Referring to FIG. 1, the "computer-generated analysis" has the following steps:

1. Analyze the audio file to get high and low level features (1)
2. Use the result of the audio analysis to determine how suitable the song is for entrainment (2)
3. Use the audio analysis and entrainment suitability analysis to generate assistive enhancements and/or modifications to the audio (3)
4. Apply the assistive enhancements to the live entrainment session, getting additional assistance cues in real time if necessary (4)
5. Learn from the results (machine learning backend) (5)

Referring to FIG. 2, the "user-verified analysis" has the following steps: analyze the audio file to get high and low-level features. Run the session using user's selected music in its original state (no cues or modifications). If the user is able to entrain to the music in its original state, no modifications are needed; continue using the song. If the user is unable to entrain to the song, proceed with entrainment suitability steps 3-4 to apply the appropriate enhancement(s). Record data from session to learn from the results (5).

(1) Audio Analysis

High Level Analysis

The audio analysis process begins by extracting high-level contextual information about a recording, such as genre, year, and origin. This information can be applied to the lower level analysis, described below to help yield more accurate results by taking into account how the music is perceived. For example, it could:

provide a tempo hint or allowed upper and lower tempo bounds to the beat tracking algorithm (see "Beat Tracking Techniques" below) based on average tempo of genre. For example, songs from the rockabilly genre often have accented $8^{th}$ note snare drum offbeats that the listener could perceive as a double-time feel. Johnny Cash's "Ring of Fire", for example, could be perceived as at 105 BPM or 210 BPM, and knowing genre context could guide the beat tracker to choose the slower choice which is in the typical range of walking cadence;

flag the song as potentially problematic, e.g., if the genre typically contains weak beat strength, irregular time signature, low rhythmic stability, (e.g. ambient, classical, experimental);

make more accurate beat tracking and downbeat estimations based on genre conventions. In reggae, for example, beats 2 and 4 are typically accented over beats 1 and 3. With this context, the beat tracker is informed to look for these weak beats which may be ignored otherwise. In rock and pop, on the other hand, the backbeat is typically on beats 2 and 4, not 1 and 3; and apply other music analysis rules, such as onset detection function weights and signal pre-processing (refer to "Beat Tracking Techniques" below);

Knowing genre may also be useful during the augmentation/enhancement step (below) as musical cues appropriate for the context can be generated.

Additionally, if the analysis returns a low entrainment suitability score, knowing the user's preferred genre would allow similar content with a higher entrainment suitability score to be recommended as an alternative selection.

Methods for obtaining high-level song data include:
using trained classification model (ML) that analyzes relevant extracted feature(s) such as MFCCs (Mel-frequency cepstral coefficients);
audio fingerprinting service (Gracenote, ARCloud, AcoustID, etc.);
third party music API metadata (Spotify, Deezer, etc.); and
User-provided metadata.

Low Level Analysis

To perform musical feature extraction, the system employs signal processing techniques from the field of Music Information Retrieval (MIR). This is an active area of research which aims to provide solutions for the automated annotation of musical features, including key, song structure, tempo, meter, loudness, and beat times. This system is primarily concerned with the analysis of rhythmic, structural, and energy features, as these are the most important indicators of whether a song can serve as a stable and strong RAS stimulus. Features extracted during the analysis stage include:

Rhythmic Features:
Average tempo (BPM)
Min and max tempo (BPM)
Local tempo values throughout song (Instantaneous BPM)
Beat times (ascending list of MM:SS:MS values, with confidence value (0.0-5.3));
Beat loudness (RMS energy at beat times)
Bar downbeat times (ascending list of MM:SS:MS values corresponding to beat one of each measure);
Time signature(s) (2/4, 3/4, 4/4, 6/8, etc., and their MM:SS:MS time range(s));
Structural Features:
Song section times (MM:SS:MS time range(s);
Duration (MM:SS:MS);
Time of first strong beat (MM:SS:MS);
Time of last strong beat (MM:SS:MS);
Detection of silence (MM:SS:MS time range(s))
Detection of fade in/fade out sections (MM:SS:MS time range(s))
Audio Signal
Left/Right channel balance (RMSE) of stereo audio file (%).
Beat Tracking Techniques Beat tracking is the process of extracting a list of times that the beat occurs within the song, the moments when a human listener would intuitively tap their foot (or entrain) to the music. This is a critical part of the system's analysis pipeline because knowledge of these times is required to measure how the patient is walking in relation to the beats of the music (see Section 4: "RUN ENTRAINMENT SESSION"). Beat tracking systems are typically implemented in multiple stages: (1) the detection of onsets (defined here as the moment a musical event such as note or drum being played becomes perceptible) followed by (2) an analysis stage that determines which of the onsets are occurring on beat by finding those with the most salient periodicity.

Onsets can be detected in a signal using a novelty function called an onset detection function (ODF). Most ODFs utilized within the art detect onsets by identifying rapid rises in energy across frequency bands (spectral energy), accomplished by transforming the original signal (time domain) into the time-frequency domain through a windowed analysis method such as the short-time Fourier transform (STFT) or wavelet transform. Other approaches exist as well, including detection of fluctuations in RMS energy (time domain). ODFs perform optimally on different types of signals, and given the inherent variation from song to song, there is no single "best" individual ODF for accurately detecting onsets in all contexts; an audio signal could represent a monophonic or polyphonic performance, and be either percussive, non-percussive, pitched percussive, or pitched non-percussive. For example, RMS energy-based approaches may work well for monophonic signals with clear percussive transients, but perform poorly on more complex polyphonic signals and signals without strong transients. Spectral energy-based ODFs on the other hand are more computationally expensive, but are effective at detecting onsets within polyphonic signals, or low-energy onsets without an attack/transient at the start of each note (i.e. a slur in a legato musical performance). They are particularly important for this system because they allow onsets to be detected in preferred music with low beat strength, and once the beat times have been determined from these detections the beat strength can be improved (see Section 3: TRACK ENHANCEMENT). For more information about an example ODF approach, see Appendix A: Beat Detection Example with DWT (Discrete Wavelet Transforms).

This system implements a flexible approach that utilizes an ensemble of ODFs, each generating its own set of detections in parallel or sequentially. This adaptive approach outperforms reliance on a single ODF, and allows a confidence measure to be calculated without the need for manually annotated ground truth beat estimates. ODFs utilized include: spectral flux, superflux, RMS energy, high frequency content, and wavelet transform. Prior to processing the signal with each ODF, an optional pre-processing step may also be implemented, such as isolating/filtering certain frequencies, or decomposing the signal into separate harmonic/percussive signals and detecting onsets from the percussive signal. After each ODF has made its detections, each set of results are evaluated by a beat tracking algorithm that estimates beat times from observed salient periodicities. Then, the level of agreement between each set of beat times is calculated based on a histogram of timing errors between each pair of beats.

The agreement scores are weighted based on a set of high level context and analysis rules that prioritize techniques that have been observed to yield higher accuracy in previous analyses of songs with similar features. For example, when analyzing music from genres likely to contain prominent off-beats such as early R&B, rockabilly, ska, Afropop, etc, more accurate beat results have been observed using an ODF capable of detecting changes in pitch ("complex spectral difference") rather than one that detect the percussive off-beats ("high frequency content"). In this case, because these detections are the basis for estimating beat times, the high frequency content ODF is more likely to estimate a set of beat times that are actually on the off-beats throughout the song. This knowledge can be applied as a series of weights when calculating the best-fit set of beat times from the candidates.

Figure 3:
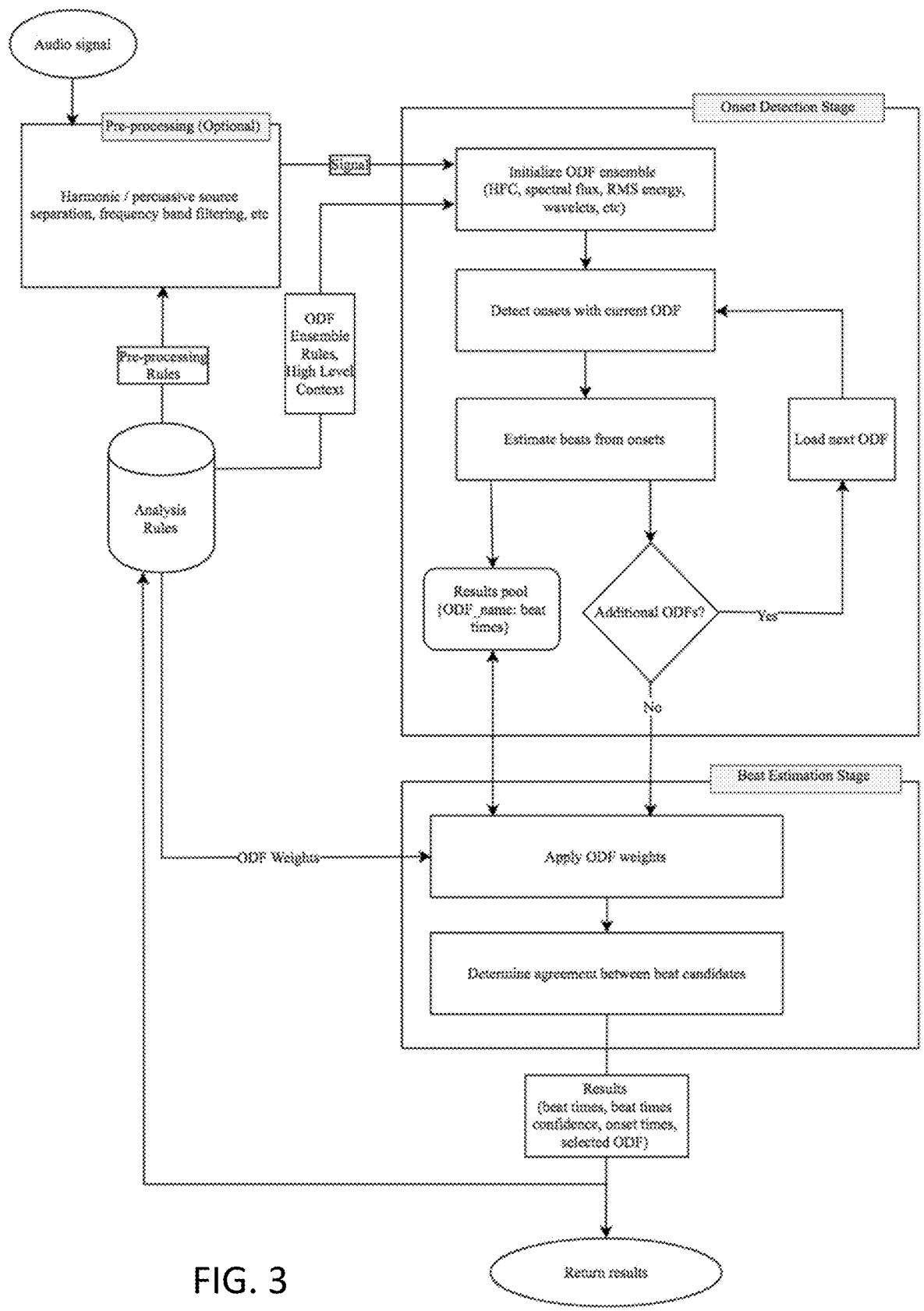
FIG. 3 is a flow chart of an exemplary embodiment of onset detection and beat tracking in accordance with the present disclosure.

This approach is shown in FIG. 3.

(2) Entrainment Suitability Analysis

Taking the audio analysis results as an input, analyze the following aspects to find the song's strengths and weaknesses and calculate an entrainment suitability (ES) score (0.0-1.0): average tempo, beat strength, beat times confidence, rhythmic stability, time signature (summary feature), tempo perception confidence, and effective duration. These results will be used to determine which, if any, track enhancements may be necessary. ES analysis is first performed on the original audio signal, but may also be used to re-analyze a signal after enhancements have been applied to check ES score impact. This technique can also be used to determine the ES of a sub-segment of the signal, for example after removing unusable intro and outro as part of structural modification.

The following is the equation for entrainment suitability, whereas the range of values from the analysis are between 0-1. A value between 0.9-1 is excellent, a value between 0.7-0.9 is useable, a value between 0.5-0.7 may require pre-enhancement, and a value less than 0.5 is rejected. This equation or a variation of this equation is used to classify different pieces of music. The time signature and average tempo numbers are represented as a binary 0 or 1 depending on whether these numbers are in the defined boundaries. The numbers signified by $y1, y2, y3, \ldots yX$, when summed are equivalent to 1 and are variable depending on the other contextual information. The other variables are represented as ranges between 0 to 1 with the best possible value equal to 1 and the worst equal to 0. The equation is as follows:

(Time signature)*(Average tempo)*($y1$*beat strength+$y2$*beat time confidence+$y3$*rhythmic stability+$y4$*tempo perception+$y5$*rhythmic ubiquity+$y6$*effective duration)

Figure 4:
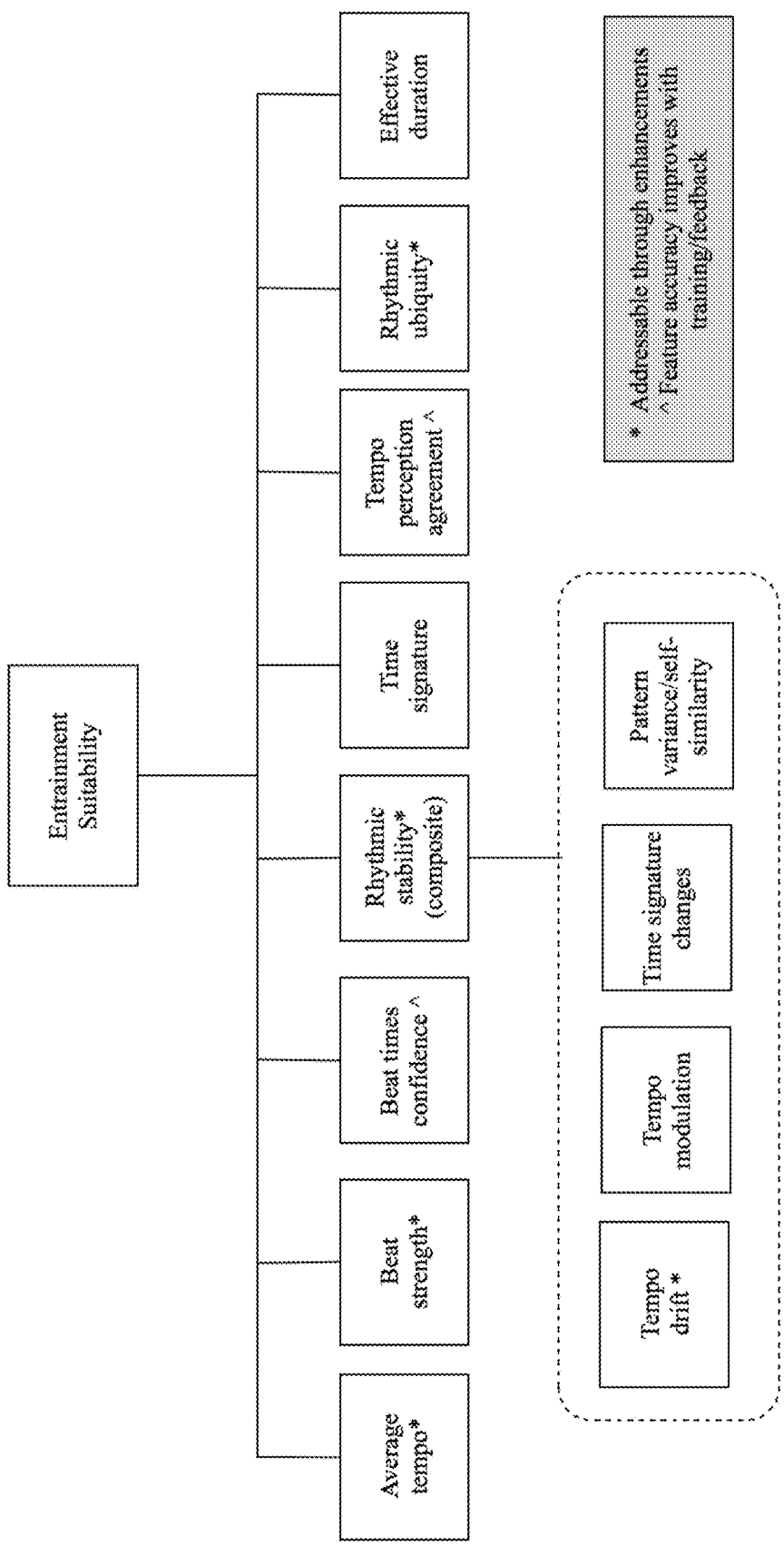
FIG. 4 is a flow chart of an exemplary embodiment of an entrainment suitability in accordance with the present disclosure.

Aspects of the entrainment suitability equation are further defined in FIG. 4 which depicts entrainment suitability.

Average Tempo

The average tempo of the song measured in beats per minute (BPM). In addition to being an important ES factor, average tempo is also useful selection criteria for choosing music to use in an RAS session. While the system is capable of time stretching music arbitrarily, the effect becomes more perceptible the further it is stretched from its native tempo, with the best results being observed within 20% of the song's native tempo. Therefore, when selecting music for use in an RAS session, the native tempo is ideally within 20% of the session cadence range.

Songs with average tempo between 60-130 (typical entrainment range) are given a score of 1.0. Score decreases logarithmically to 20 BPM outside of these bounds, where 40 and 150 are assigned a score of 0.0.

Enhancement Strategy:

Music can be time shifted by a constant factor, bringing average BPM into entrainment range or to user's target entrainment cadence.

Beat Strength

Figure 5:
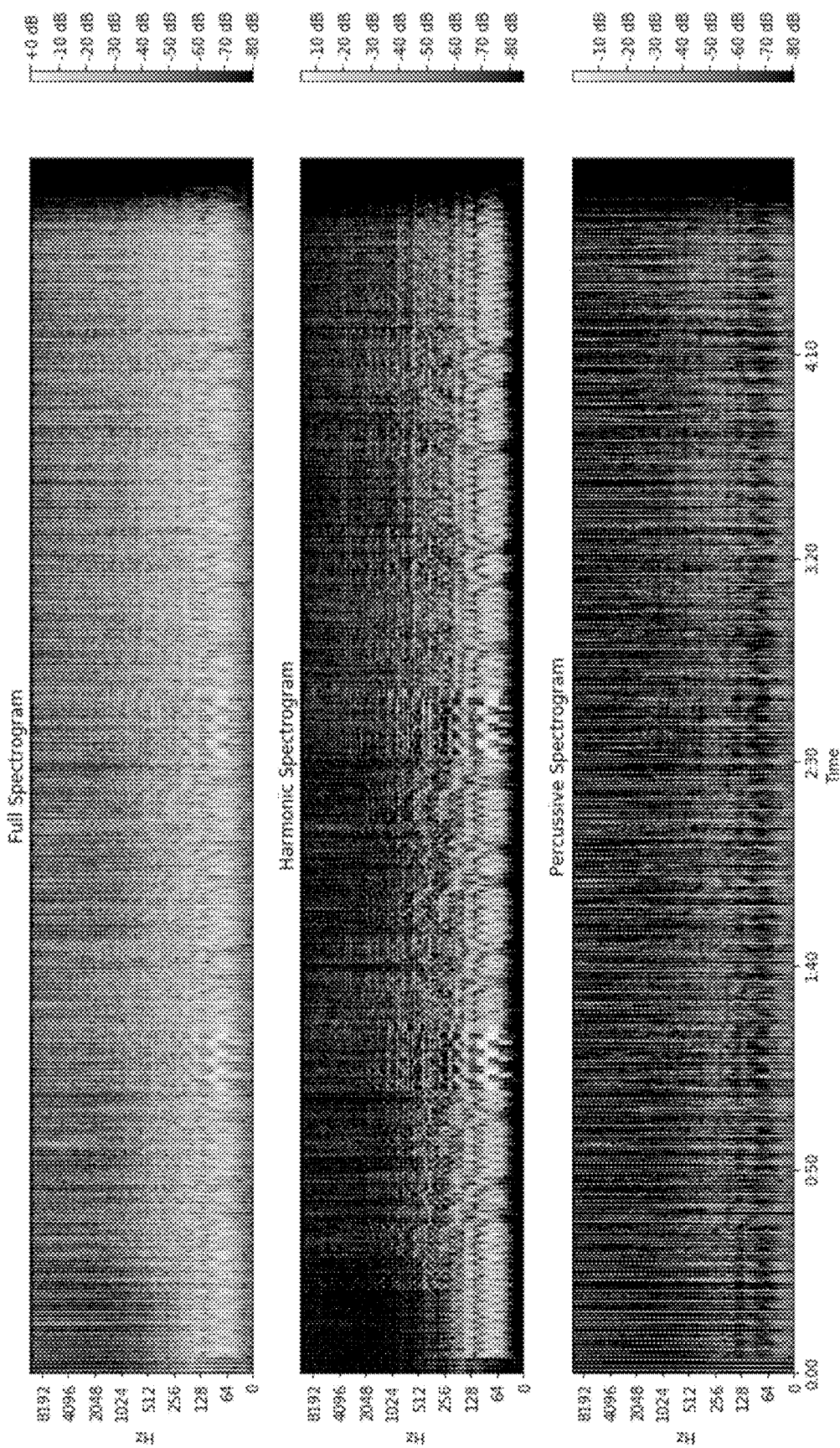
FIG. 5 is a depiction of beat strength in accordance with the present disclosure.

As depicted in FIG. 5, RMSE at detected beat times (song median), scaled linearly to 0.0-1.0. More prominent perceived beat loudness is better as an RAS stimulus, often indicative of the beat being played by a percussive musical part. 1 is greatest strength, 0 is weakest.

The following example, "Billie Jean" by Michael Jackson, is an example of high beat strength, as indicated by the energy within the percussive spectrogram (displays percussive components of the signal as instants with energy vertically spanning multiple frequency bins).

Enhancement Strategy:

Beat strength enhancement strategies discussed in detail in Section 3. These include adding a musical cue at the beat times.

Beat Times Confidence

Beat times confidence score is returned from the beat tracking stage of the music analysis, based on the agreement level between the beats derived from each set of ODF detections. Higher score indicates better suitability because multiple approaches detected similar prominent rhythmic pulse, which often indicates song has unambiguous rhythmic and timing features.

The beat times confidence score maps to ES score values as follows: 0.0-1.5 is deemed low confidence and is assigned a score of 0.1.5-3.5 indicates good confidence, and is assigned a score of 0.5. 3.5 to 5.3 indicates excellent confidence and is assigned a score of 1.0.

Enhancement Strategy:

Confidence score could improve as a side effect of (re-) analysis and beat tracking improvements, such as ODF weights and pre-processing steps.

Time Signature

Average time signature of the song (summary feature). For tasks that are binary in nature, duple or quadruple meter is recommended (e.g. 2/4, 4/4, 6/8). Score of 1 given if song has an allowed time signature, 0 otherwise.

Enhancement Strategy:

N/A. Time signature is integral part of song composition and if problematic the song should not be used.

Tempo Perception Agreement

Agreement level of estimated tempo, as determined by observed user entrainment data. A common problem in tempo detection is its inherent subjectivity, and a known issue is the "octave error" in which some listeners may detect the beat at half or double the rate of another listener. Tempo estimated by system should match the tempo perceived by human listeners.

Potential values are either 0 or 1 with agreement to the tempo being a 1 and half time and/or double time being a 0. This is most likely used and factored in the re-analysis of a song because it is largely based on user-observed data.

Enhancement Strategy:

Accuracy of this detection will improve with user-observed data.

Rhythmic Ubiquity

Percentage of song duration with prominent rhythmic elements present. Presence of rhythmic parts better for entrainment as these are effectively the RAS stimulus. Rhythmic parts dropping out of song can disrupt flow and make beat times more difficult to detect (lower beat times confidence score). One approach for measuring ubiquity within a song is detecting presence of percussive elements in percussive spectrogram (see FIGS. 6-8).

Score ranges from 0.0 (0% rhythmic ubiquity) to 1.0 (100% rhythmic ubiquity).

Enhancement Strategy:

Cue may be added to section with known confident beat times but low beat strength, thereby increasing overall ubiquity of rhythmic parts.

EXAMPLES

As mentioned previously "Uptown Funk" contains constant, percussive parts from start to finish, and therefore has a high rhythmic ubiquity score of 1.0. Of particular interest are the high magnitude broadband spikes in the percussive spectrogram. Even in the intro section (0:00-0:16) where the magnitude of the spikes is lower, the percussive part is present and discernable.

Figure 9:
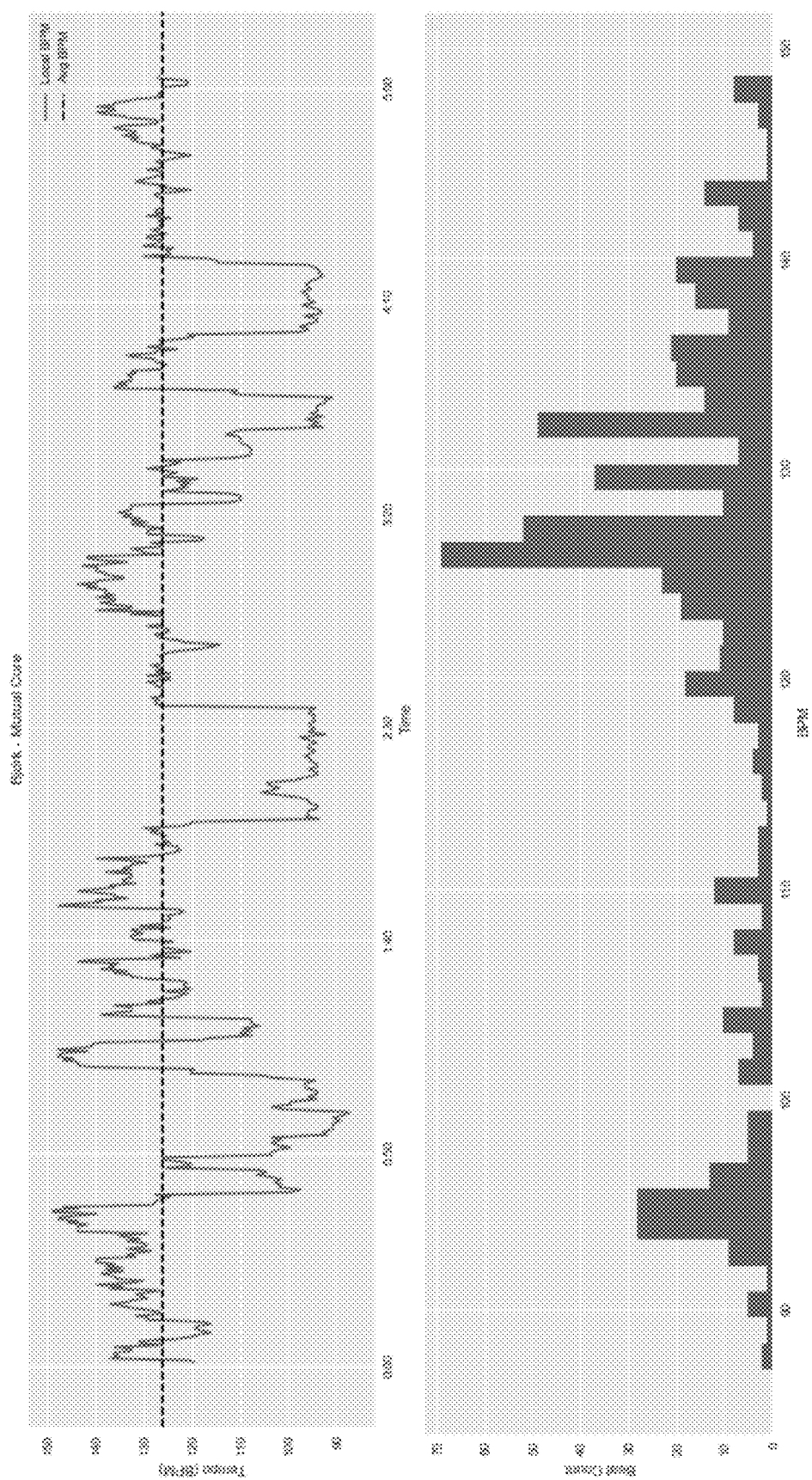
FIG. 9 is a depiction of high tempo drift (bad) during an exemplary embodiment playing "Mutual Core" by Bjork.

As shown in FIG. 9, an example of a song with low rhythmic ubiquity is "Mutual Core" by Bjork. This song has two distinct sections containing rhythmic parts, but they only comprise 60 of the 306 second song duration (20%), yielding a low rhythmic ubiquity score of 0.2.

Effective Duration

The amount of usable time in seconds, after unsuitable, unaddressable sections are removed must be at least 60 seconds in duration. This condition ensures that edge case short songs are not used ("Let Me Down Up On It" by Tom Waits, which is only 0:53 in duration), and that a sufficient length exists if a structural modification has been applied. Score of 1.0 is given if usable song duration is greater than or equal to the 60 second minimum threshold, 0.0 otherwise.

Enhancement Strategy:

N/A. If audio signal is not long enough to be used, another selection should be used.

Rhythmic Stability

Rhythmic stability is a composite score (0.0-1.0) that indicates the amount of variance of rhythmic/metric aspects during the song, taking into account tempo drift, tempo modulations, time signature changes, and rhythmic pattern variance.

The value of rhythmic stability is between 0 and 1 with 1 being the best and 0 being the worst. Higher rhythmic stability indicates less fluctuation, and therefore more suitable content for use in an RAS session. The equation includes x1, x2, x3, . . . xZ, as weights that sum to 1 that multiply by all of the factors of rhythmic stability A1, A2, A3 . . . . Az, which are numbers between 0 and 1.

$$\text{Rhythmic stability} = x1*A1 + x2*A2 + x2*A3 + x3*A3 + \ldots xZ*AZ$$

Enhancement Strategy:

Tempo drift may be reduced through audio quantization. Problematic section(s) may be skipped, only using suitable sections(s) of a song.

Rhythmic Stability Factors

1. Tempo Drift—A1

Measured as 1.0-X % of beat delta times within allowed perceptible variance band from the median beat delta where 100% variance has a score of 0 (1.0-1.0), and 0% variance has a score of 1.0 (1.0-0.0).

Some tempo fluctuation is normal in any human musical performance, especially if it was not recorded using a click track or computer-sequenced accompaniment (e.g. drum machine, digital audio workstation, etc). Wide fluctuations will contribute to a low tempo stability score. "Thousand" by Moby is an extreme example of high tempo variance, which has a tempo that varies constantly throughout its duration, peaking around 1,000 BPM.

Figure 8:
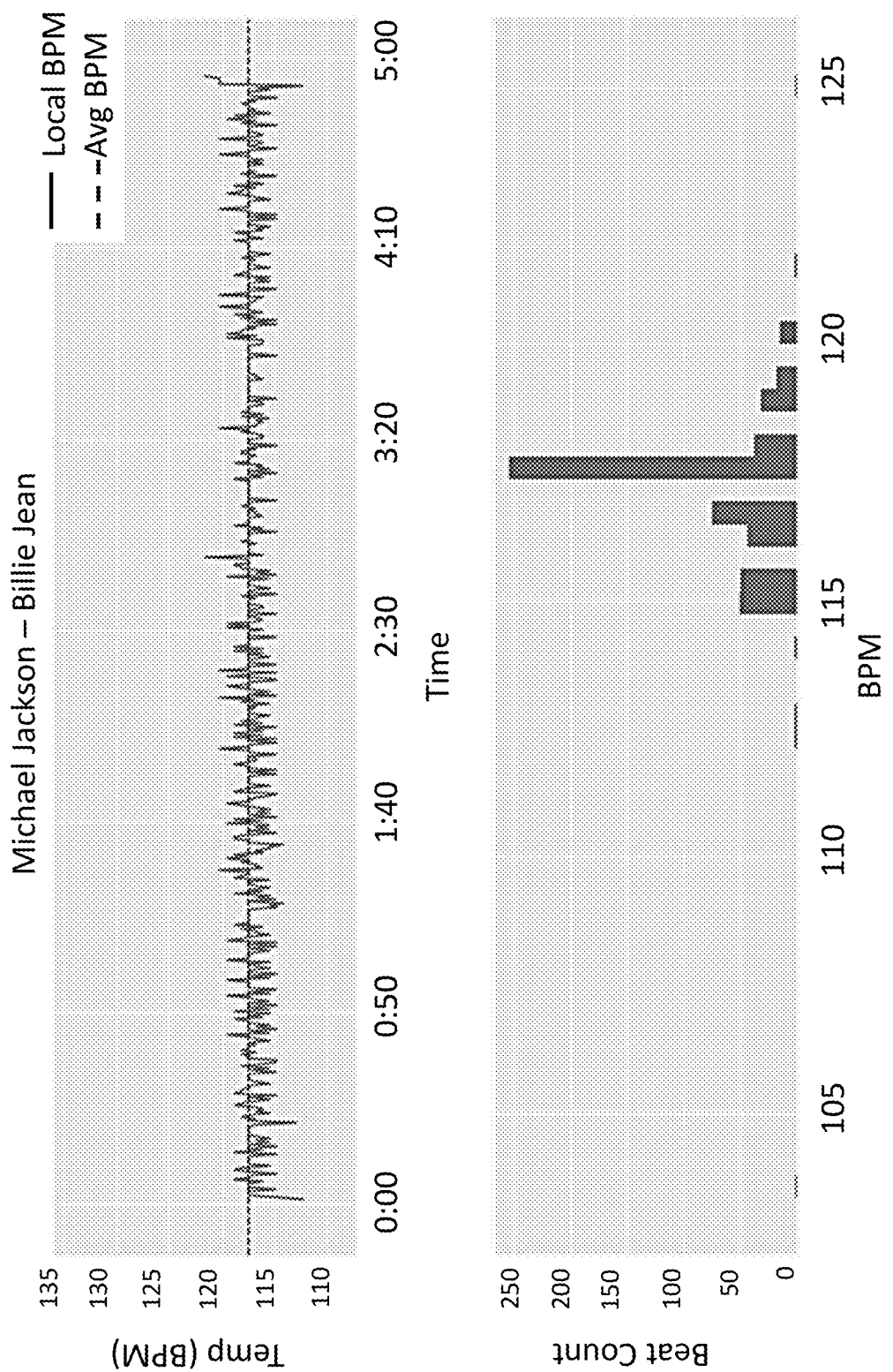
FIG. 8 is a depiction of low tempo drift (good) during an exemplary embodiment playing "Billie Jean" by Michael Jackson.

The following are musical examples of gradual tempo changes that may occur, as depicted in FIGS. 8-9:
    ritardando: slowing down
    accelerando: speeding up
    rubato: musician taking liberty with tempo to play expressively (tempo may fluctuate with musical phrasing)

2. Tempo Modulation—A2

When the song tempo suddenly increases or decreases by more than 5% from the original tempo, and the new tempo is sustained. Tempo changes ranging from 5%-25% are deemed addressable through time shifting: Changes of 0-5% are assigned a score of 1. From 5 to 25% change the score decreases linearly, where 25% and greater is assigned a score of 0.

One type of tempo modulation is "metric modulation", where a tempo and/or meter change by recontextualizing the current beat or a grouping of beat subdivisions as another pulse value. An example of this can be heard in Arcade Fire's "Here Comes the Night", where the tempo suddenly changes from ~95 to ~145 BPM at 4:36, with the impact of a 3/16 note grouping at 95 BPM becoming the new quarter note at 145 (tempo increase of 1.5×).

Figure 10:
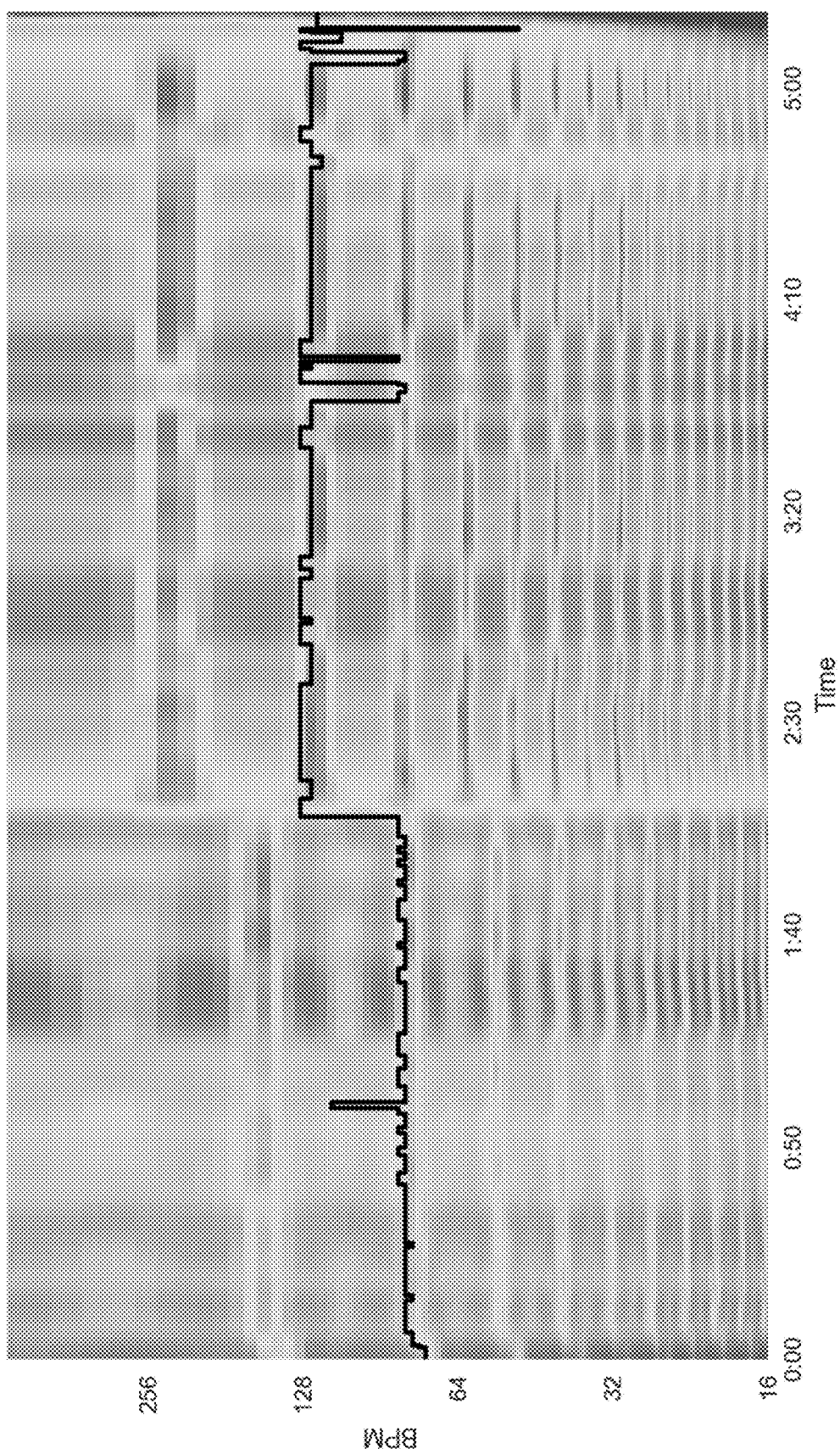
FIG. 10 is a depiction of an exemplary tempo modulation in accordance with the present disclosure.

An example of a tempo modulation, as shown in FIG. 10, not related by a metrical pulse can is shown in following tempogram of "Band on the Run" by Paul McCartney and Wings. At 2:14, the tempo suddenly changes from 81 BPM to 127 BPM, a 57% increase. The line represents the local tempo value. In this case, a structural modification could be made that would permit part of the song to be used in the session, either the time region prior to or after the tempo change (see "Structural Modifications" within section 3 below).

3. Time Signature Changes—A3

A time signature change is when a song shifts from one time signature to another mid-song, for any duration. Assuming a song begins in 4/4 time, a single measure containing an odd number of beats, such as 3/4, would reverse the left/right synchronicity of binary movement with the phase of the music (assuming musical phrasing is aligned with the bar structure). This type of shift in a song is a binary disqualifying event and is assigned a score of 0. Absence of time signature changes is assigned a score of 1.

"Happiness is a Warm Gun" by the Beatles exemplifies problematic time signature changes, as the song begins in 4/4 time, but later shifts to alternating measures in 9/8 and 10/8 time.

4. Rhythmic Pattern Variance—A4

Rhythmic pattern variance is a measure of the similarity of adjacent patterns in a song, and can be obtained with techniques such as detrended fluctuation analysis (DFA) or autocorrelation of inter-onset intervals. A song with high rhythmic patterns homogeneity is for better rhythmic stability.

A song with perfect homogeneity (100%) is given a value of 1, while a song with no homogeneity (0%) is given a value of 0. Note, a value of 0 in practice is not practical, as random homogeneity is often greater than 30%.

The aforementioned equations can be informed and edited by training data provided by a person tagging analyzed data with their perspectives on these various parameters, either ranking if they are in agreement or disagreement with the ES analysis or providing details on how they would rate the song on these various parameters.

(3) Track Enhancement

Combining audio analysis data and knowledge of the song's strengths and weaknesses for entrainment, a song's entrainment suitability may be improved through the creation of assistive cues, modifications to the audio signal, and minor changes to the song's structure. One or more of these strategies may be applied at a time (e.g. a cue may overlay the music as it is being quantized). See FIG. 1 steps 3-4 and FIG. 2 steps 3-4.

Musical Cues

Defined broadly, a "musical cue" is a sound added during playback that augments the original song. Types of musical cues include the following:

- Single beat musical cue which plays on each beat (quarter note), or plays on each beat plus subdivisions like eighth or sixteenth notes. Subdivided notes may be helpful for perceiving time intervals between beats at a slow tempo, and should be quieter (unaccented) than the note that plays on beat to ensure that the beat remains accented. This cue could be any percussive sound, from a standard metronome woodblock or clave-like "click" to a genre-appropriate percussion sound or a low frequency bass drum. Non-pitched sounds with prominent transients are the preferable timbre and shape, as pitched sounds may lead to dissonance that detracts from the user's enjoyment of the music, or a weak onset that causes the sound to be imperceptible. Pitched sounds may be used with knowledge of song key.
- Drum pattern synced with the playback of the original song, implemented as either individual samples triggered via MIDI or an audio drum loop. In order to properly sync a. drum pattern that is longer than one beat, the bar-level ("downbeat") times must be known, in addition to the remaining bar beat times. The downbeats serve as anchor points, aligning the pattern in time with the original music. They also serve as reference points for re-establishing synchronization with the song if it is lost.
- Voice counting beats during playback, or counting down to the first beats to instill the tempo in the listener ("priming"). Voice could also instruct user to listen to song for period of time before starting repetitive motion activity.

Mix balance between original audio signal and aforementioned musical cues varies depending on how much assistance is required. When non-entrainment is initially detected a subtle amount of the cue may be introduced (less than 50% balance), leaving the original audio as the primary stimulus. If non-entrainment continues the next enhancement is generated, such as a rule for the audio engine to increasing the mix percentage of the cue in relation to the music. Likewise, following a period of successful entrainment, a possible rule would he to revert to the prior cue mix level where less assistance is required.

The following graphs show the impact of adding musical cues to music.

Figure 11:
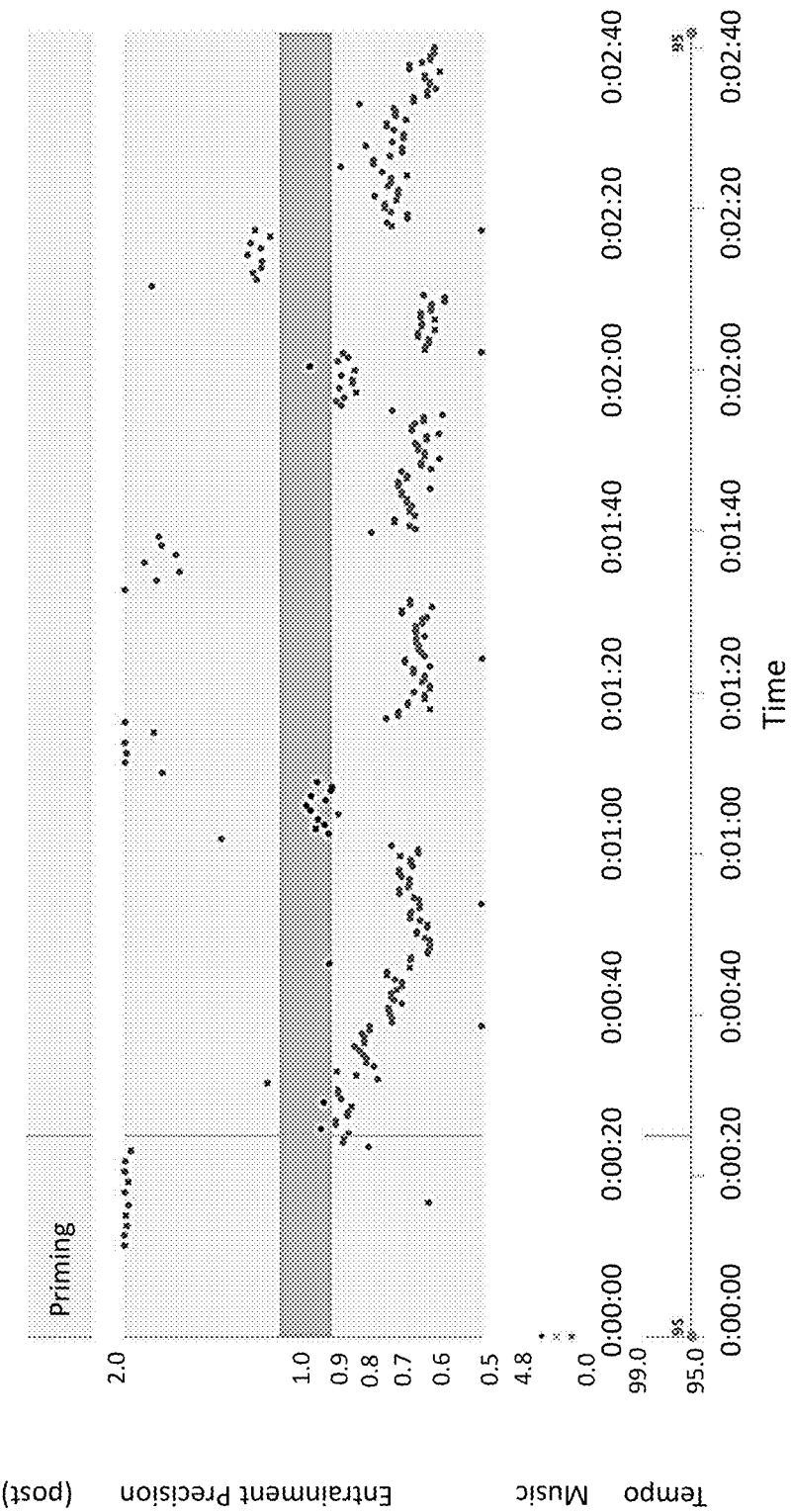
FIG. 11 is a depiction of an exemplary patient movement without assistance cues in accordance with the present disclosure.

First, FIG. 11 shows the result of a session in which a human participating was asked to walk to the beat of a piece of music with low beat strength, and a chart of their results (see Section 4) was calculated. The accuracy was poor, as signified by the light grey dots outside of the horizontal center band representing successful entrainment bounds. No assistance cues were applied during this session.

Figure 12:
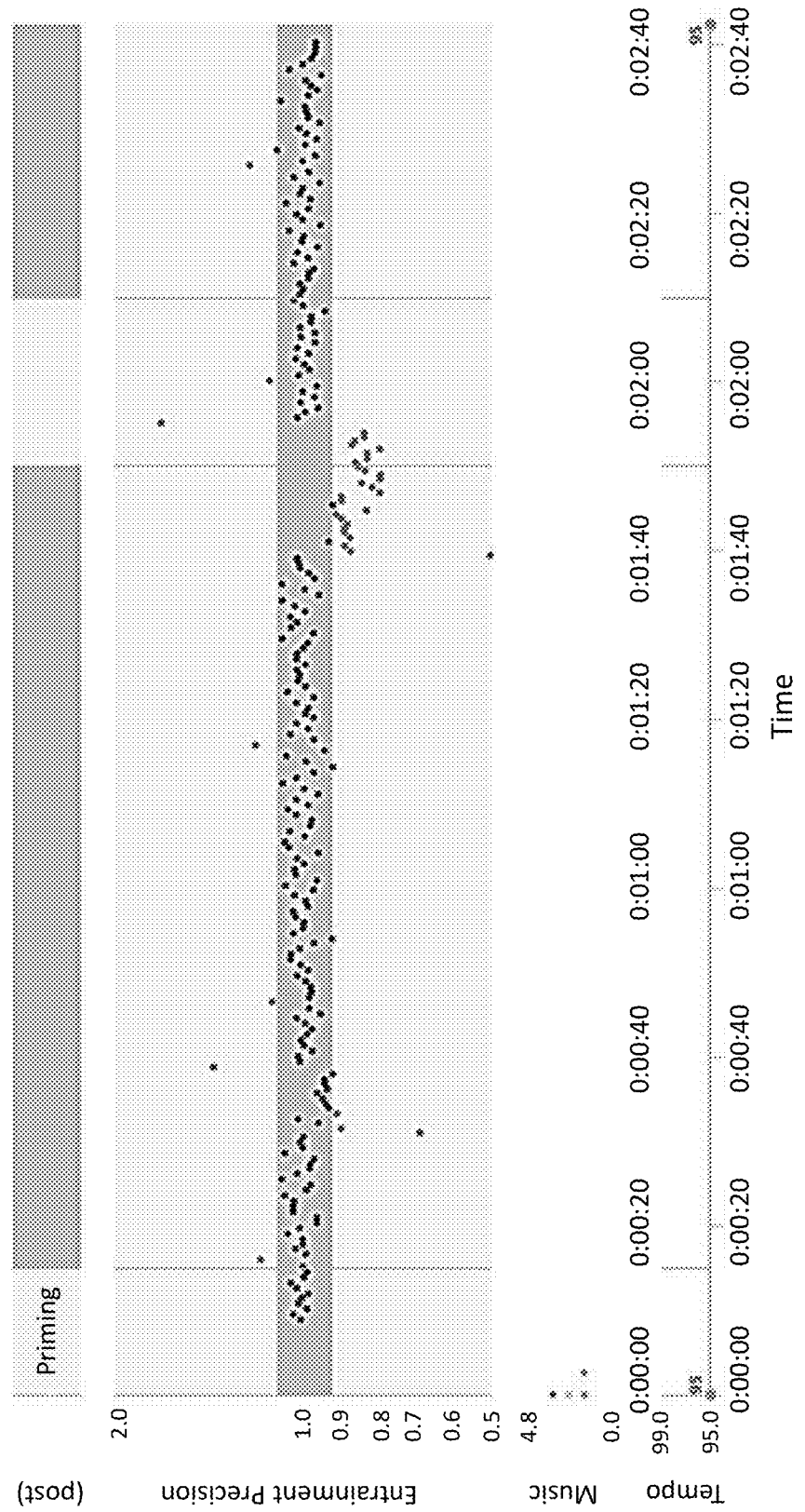
FIG. 12 is a depiction of an exemplary patient movement with assistance cues in accordance with the present disclosure.

The next graph, FIG. 12, is the same subject moving to the same song, but instead with the addition of a musical cue added to strengthen the beat signals per the Computer-Generated Analysis (see FIG. 1). As observed, the accuracy of the walker improved, while still getting to listen to their preferred piece of music.

Figure 13:
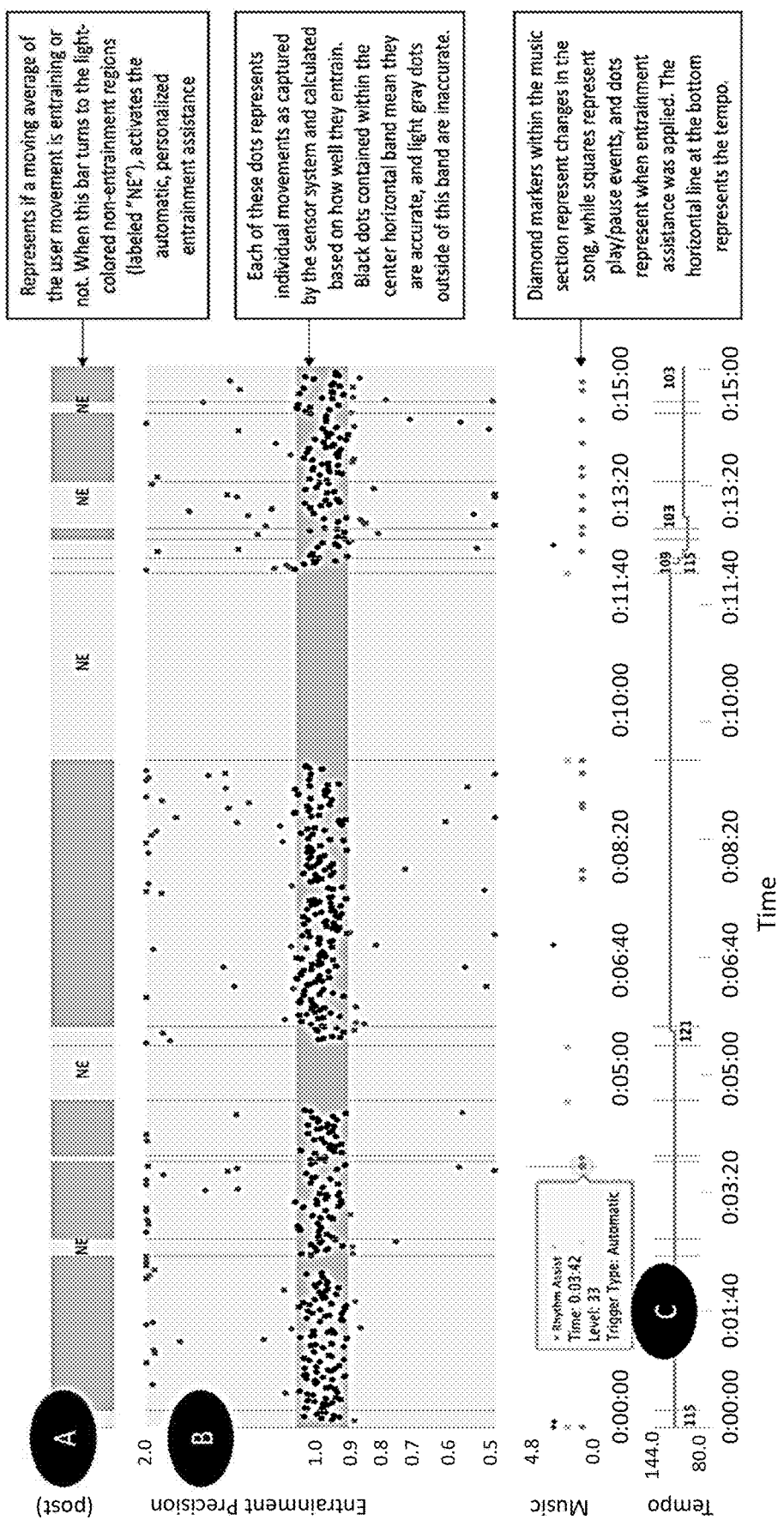
FIG. 13 is a depiction of an exemplary embodiment wherein assistance cues are generated during session in accordance with the present disclosure.

The next graph, FIG. 13, shows entrainment assistance being applied during an entrainment session (see FIG. 2). This graph shows when a user movement is not entraining (Section B), a moving average of that entrainment (Section A), which when dark grey is good and when light grey ("NE" indicating non-entrainment) a correction added and recorded as shown in Section C.

Figure 14:
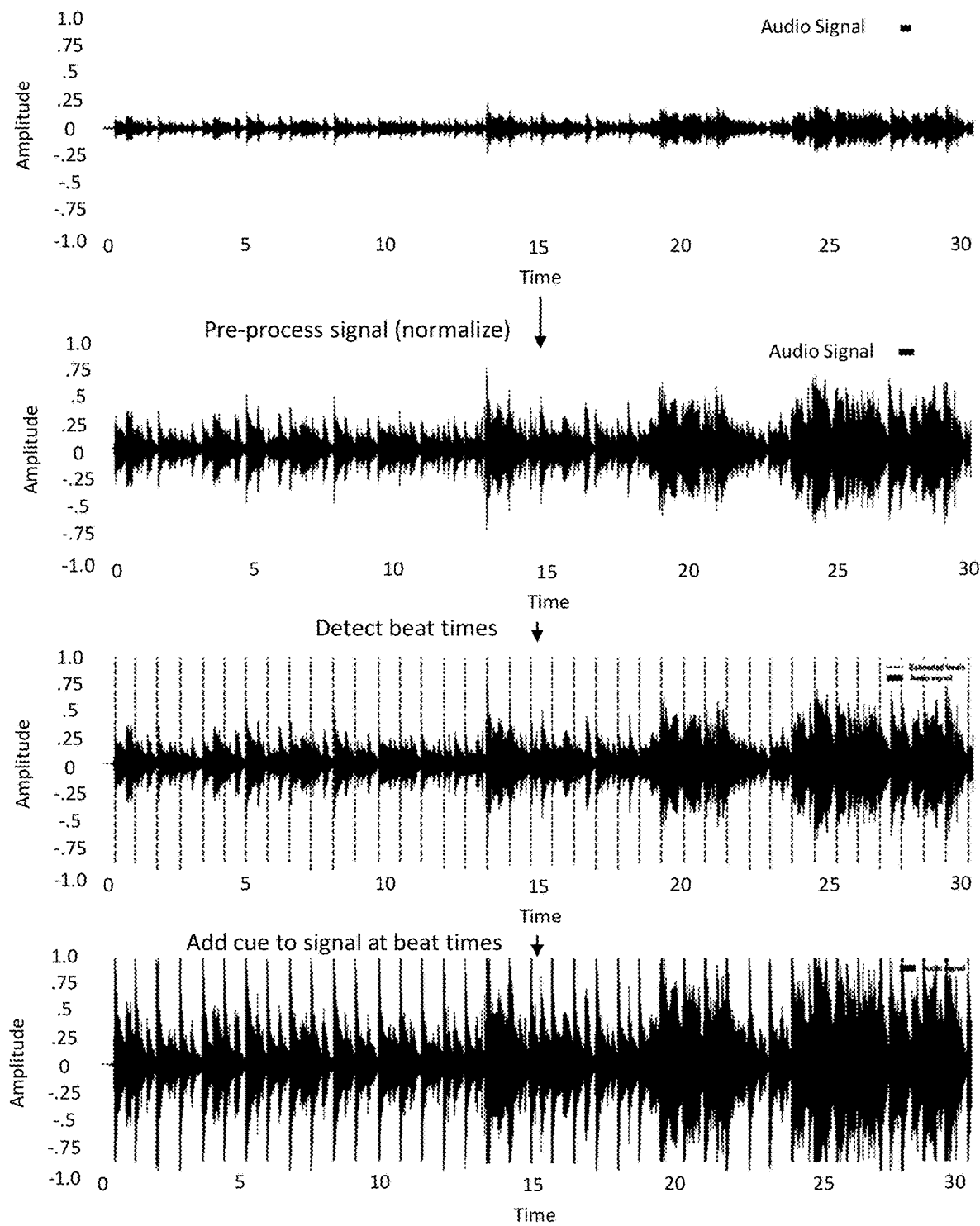
FIG. 14 is a depiction of an exemplary addition of percussive cue at beat times in accordance with the present disclosure.

Cues can be added in the following ways:

First, musical cue at beat position: adding a musical cue where the beat signal is determined to be. Adding this musical cue improves the strength of the beat signal, improving its ability to be used in a therapeutic session. This process is shown in FIG. 14 First, the original audio signal is loaded. In this case, the original signal is weak as indicated by its low overall amplitude. A simple pre-processing step in this case is to apply normalization, which increases the signal amplitude by constant amount. Beat times are estimated from the normalized signal, and lastly a percussive cue is added at the beat times to create a new composite signal.

Figure 6:
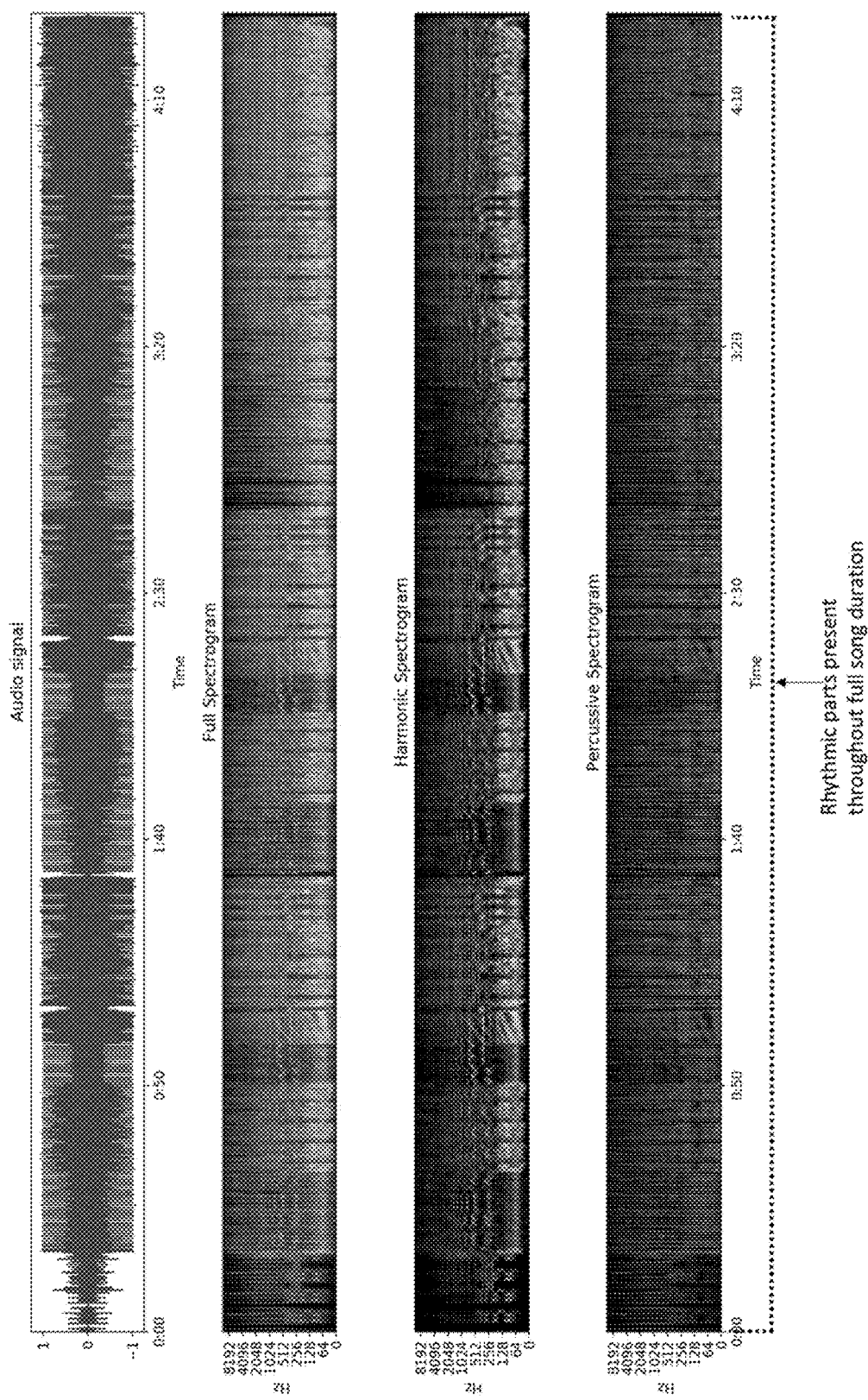
FIG. 6 is a depiction of high rhythmic ubiquity in accordance with the present disclosure.
Figure 7:
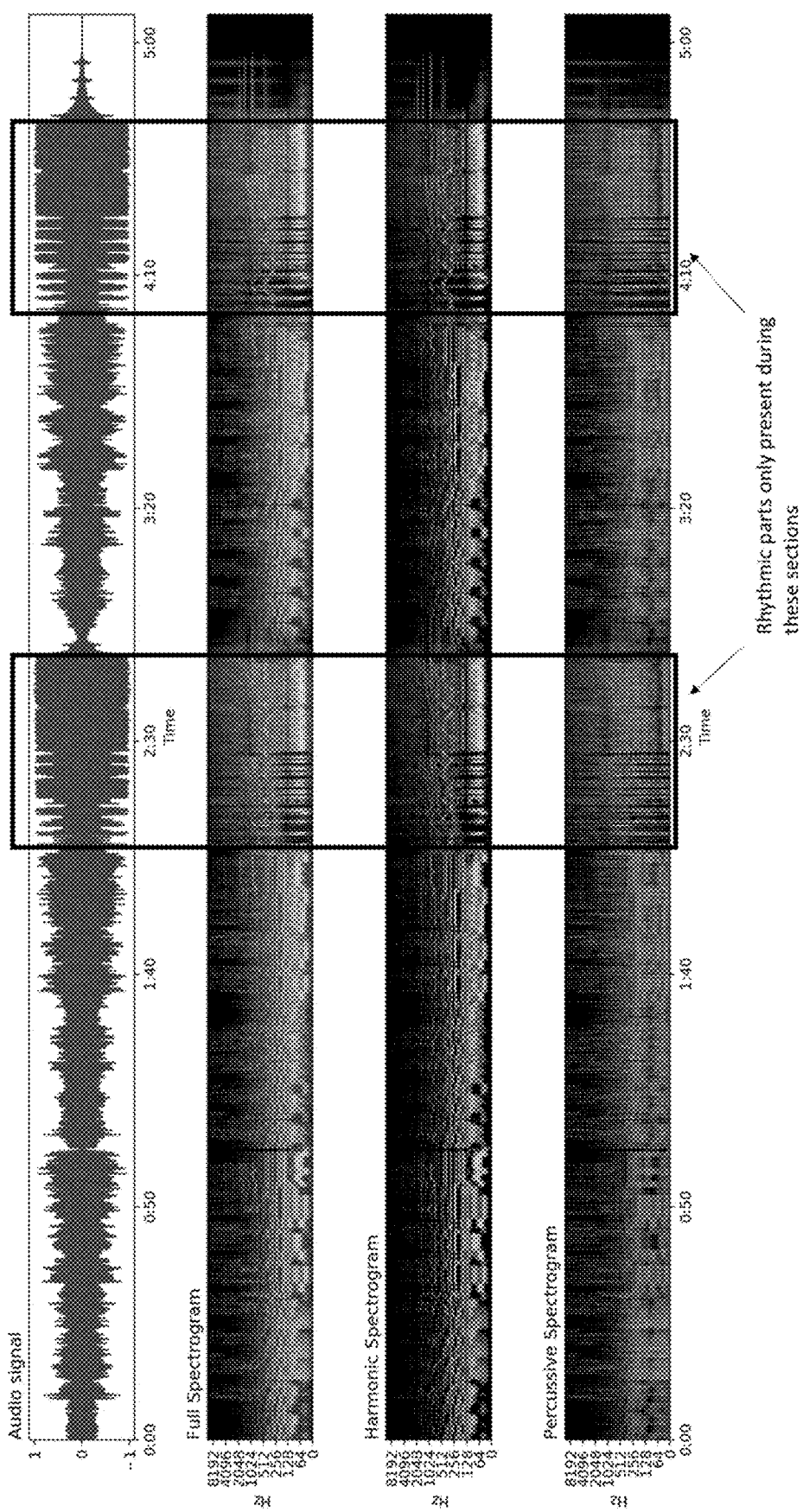
FIG. 7 is a depiction of low rhythmic ubiquity in accordance with the present disclosure.

The decision to add the musical cue can be made during the song when the person has a difficult time entraining to the beat as shown in FIG. 6 above. This can also be decided in advance if the song is determined to have a low beat strength or rhythmic stability as described in FIG. 5 above.

Second, musical cue on the same side as step: similar to above, but instead, add the musical cue only to the side that is making the next movement as determined by the sensor inputs (e.g. if a right step is expected then the metronome will play in the headphones in the right ear). This increases the cognitive load to the person and improves their perception of the beat on that side.

Third, musical cue on opposite side of Step: Similar to above, but instead, adding a musical cue to the ear that is opposite to the side of the step. This is done with headphones to isolate the sound for delivery, however can also be performed with high fidelity surround sound systems. The impetus for this is discussed below in the Appendix B, "Motor, Music, and the Brain".

Fourth, musical cue with Low Rhythmic Stability: Adding a musical cue to parts of the song that have low rhythmic stability. For example, adding cue to emphasize strong beats instead of syncopation, which some listeners may find distracting in entrainment context.

Fifth, priming cue: before the session begins play a count-off cue (either speech or metronome) to instill the beat in the listener, and allow them to effectively anticipate their first steps. An accompanying voice cue can also be implemented to count off the beats, to give feedback as it relates to the beats, and to instruct the user to wait until a certain segment of beats is completed.

Audio Signal Modifications

Whereas a musical cue augments the existing song by overlaying additional sounds, suitability can also be improved by processing the audio signal directly:

First, emphasize the song's drum part through equalization (boosting and attenuating frequencies in the harmonic spectrum). This may be particularly effective in cases where beat time confidence is low, but there is still a clear drum track. Frequency modifications can be made to the audio file itself and re-rendered, or applied as real time EQ using the session's audio engine.

Second emphasize the song's drum part through drum reinforcement techniques, whereby the timestamps of individual drum occurrences (kick, snare, high hats, etc.) within the original audio signal or separated percussive source are estimated by a classifier model trained to identify individual drum sounds based on spectral content. With the knowledge of the times that these drum sounds occur in the original song, a reinforcement track can be generated and mixed with the original song to improve the beat strength of the original drum pattern played.

Third, re-mix the song: extract percussive and harmonic sources, then re-mix the sources together, changing the balance to emphasize the percussive source to increase the perceived beat strength.

Figure 15:
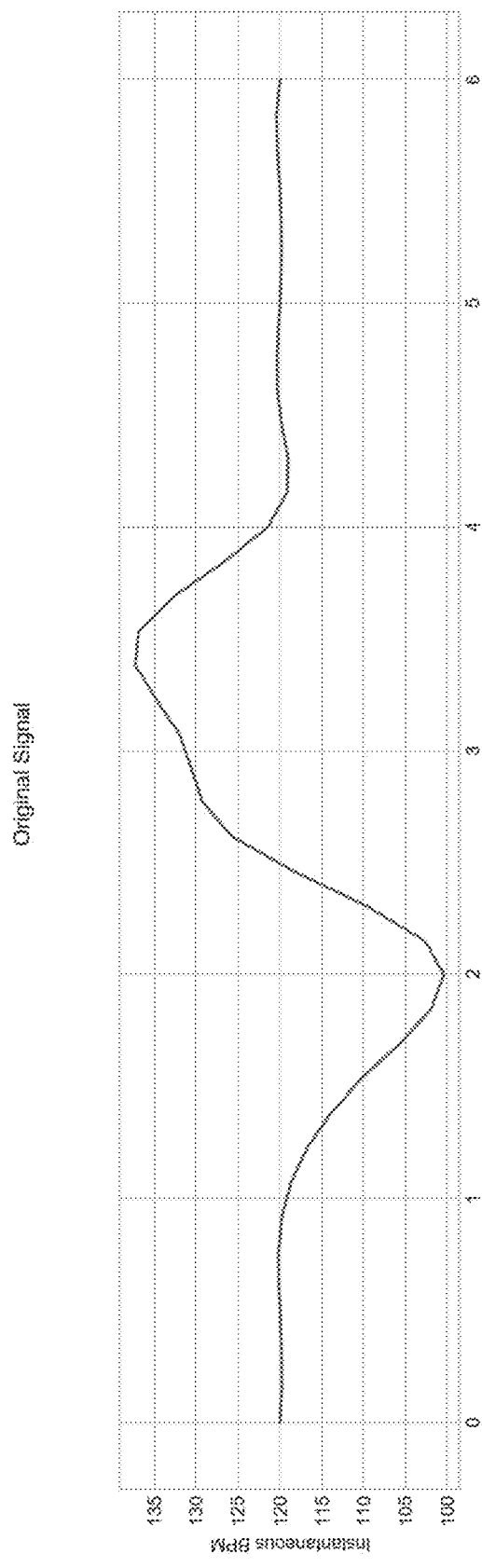
FIG. 15 is a depiction of an exemplary embodiment of a drum loop (pre-quantization) in accordance with the present disclosure.
Figure 15:
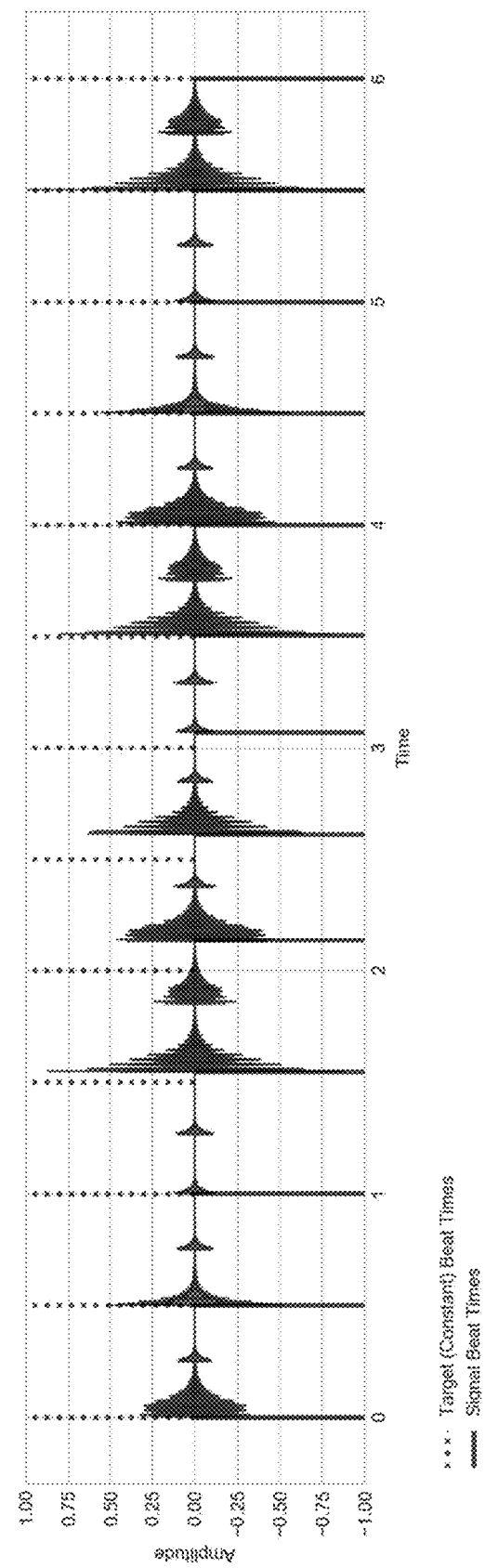

Fourth, quantize the audio to reduce minor fluctuations in tempo and make beat timing more precise. This can be accomplished by time stretching the signal at various metrical reference levels (beat, bar, etc) by aligning the reference beat locations with an underlying grid of the ideal constant beat times. For example, in a live drum performance, the audio could be quantized to ensure that a bass drum hit occurs precisely on beat one and the snare drum occurs precisely on beats two and four. This is exemplified in FIGS. 15 and 16.

Figure 16:
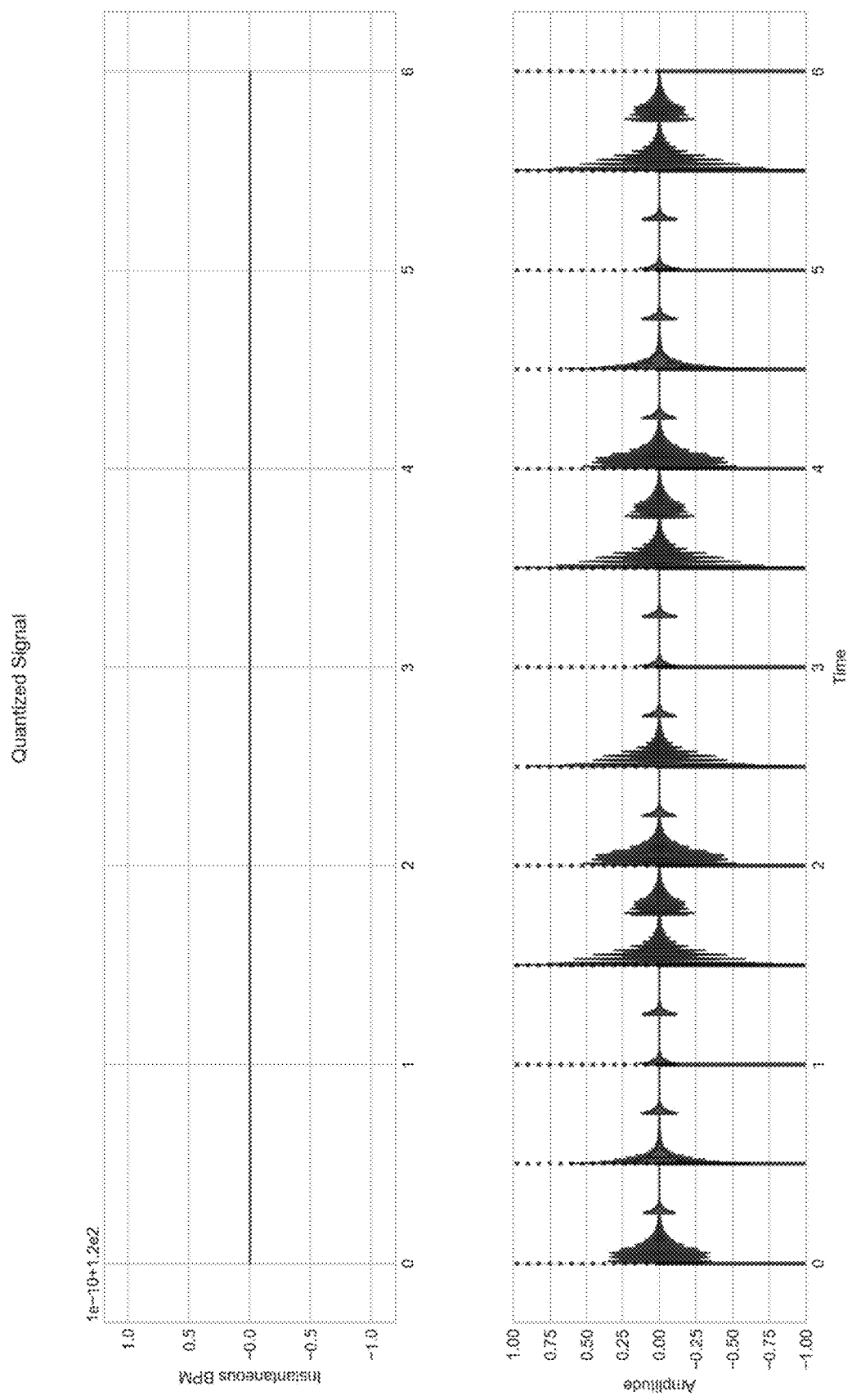
FIG. 16 is a depiction of an exemplary embodiment of a drum loop (with per-beat quantization) in accordance with the present disclosure.

Observe how the instantaneous BPM (60/beat2−beat1) is impacted by varying the beat time intervals in the drum part, first playing at a slower rate than the target, then faster. The process of applying per-beat quantization can remove this fluctuation, resulting in a "flattened" tempo as shown in FIG. 16.

Note that programmatically altering music in this manner may remove the groove or "feel" of the music, and depending on the quantization amount applied, a user may notice the difference, particularly with familiar music. To accommodate this technique while recognizing the potential negative perceived impact, quantization may be applied in varying degrees (e.g. time stretch by 25%, 50%, 75%, 100% toward the constant grid beat time).

Fifth, normalize songs to increase the loudness of the signal based on peak or average RMS loudness. This step is useful for pre-processing quiet songs, and so that songs played consecutively within a session playlist have approximately the same loudness. Applying normalization based on the signal's max peak will ensure that relative dynamics of the song are not impacted.

Sixth, reduce stereo image width (the perceived width of left/right audio signal distribution) or create mono mix combining both left and right channels if song contains extreme stereo panning. In particular, drums mixed entirely left or right may be distracting or contribute to low beat strength, such as "Nowhere Man" by the Beatles, in which the drum track is mixed almost entirely in the left channel. This is also an important consideration because the assumption should not be made that all listeners have equal or perfect hearing in both ears. To address this accessibility consideration, the system may be configured to mix down to mono on a per-user basis.

Structural Modifications

The structure of a song may also be modified to improve entrainment suitability by skipping unusable regions of the song, provided that the remaining duration and structure still function as a suitable stimulus. Typically, the removed sections occur at the start or end of a song, so as to preserve as much of the song in its original form as possible. Examples of unusable sections include: fade-in/fade-outs, silence, non-music such as speech or applause, rubato tempo, isolated time signature changes, and sections without a rhythmic pulse.

Figure 17:
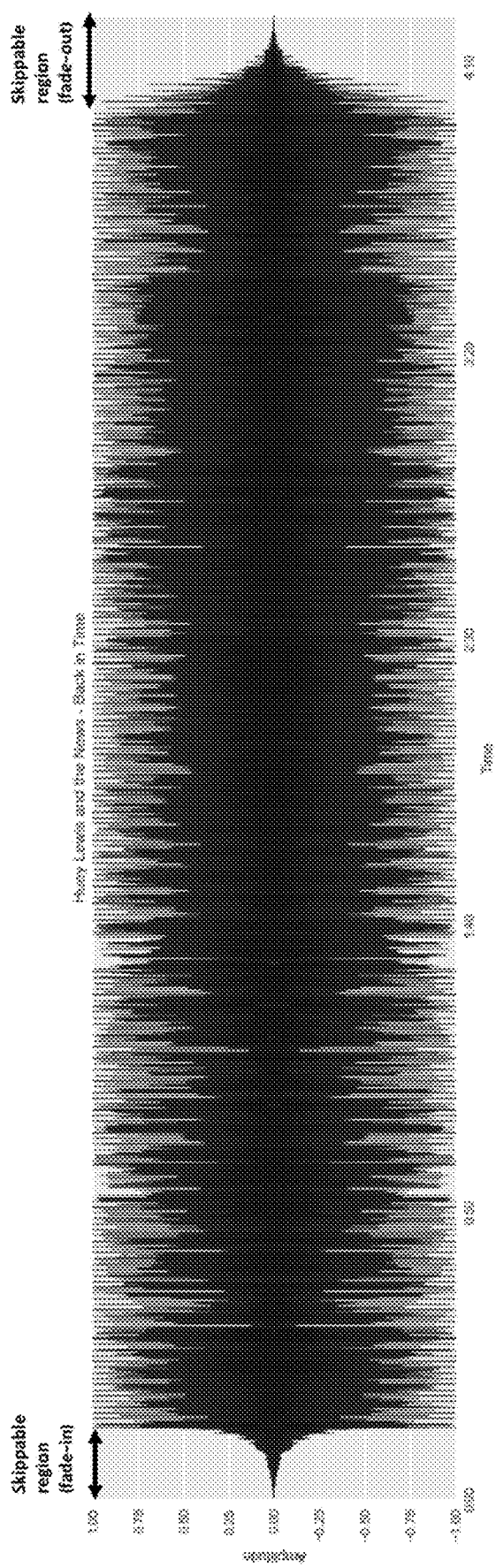
FIG. 17 is a depiction of an exemplary embodiment of structural modification in accordance with the present disclosure.

The following example, depicted in FIG. 17, shows how a song containing both a fade in and fade out ("Back in Time" by Huey Lewis and the News begins), could be addressed with a structural modification. First, these time regions are detected during the music analysis as continuous sequences of directional changes in RMS energy. As shown in the following waveform plot, the fade-in occurs from 0:00-0:12 and the fade-out occurs from 4:03-4:19.

This song could be improved for use in a session by (1) locating the beat times closest to these two reference points and (2) providing them to the audio engine as cue points or producing a new version of the signal that skips these time regions. In effect, the song would then begin at the first strong beat, the downbeat at 0:12, and end before the signal fades to silence, beginning at 4:03.

In order to ensure that modifications are aligned with musically-relevant timing, beat-synchronous song sections boundaries must be detected. During the low-level analysis, the signal is segmented into perceptually-relevant song sections, which in rock and pop genres often correspond to distinct sections like verse, chorus, bridge, etc. For this task, a homogeneity-based method such as clustering using MFCCs may be used, which effectively groups sections based on harmony, timbre, and instrumentation. This process is performed as a windowed analysis and therefore the detected segment boundaries will likely not align exactly with perceived musical section boundaries. With prior knowledge of the song's beat times and meter structure the segment boundaries can be adjusted to the nearest beat or downbeat.

The suitability of a resulting section after omitting unusable section(s) may be evaluated by performing an additional entrainment suitability analysis on the resulting section.

(4) Run Entrainment Session

Figure 18:
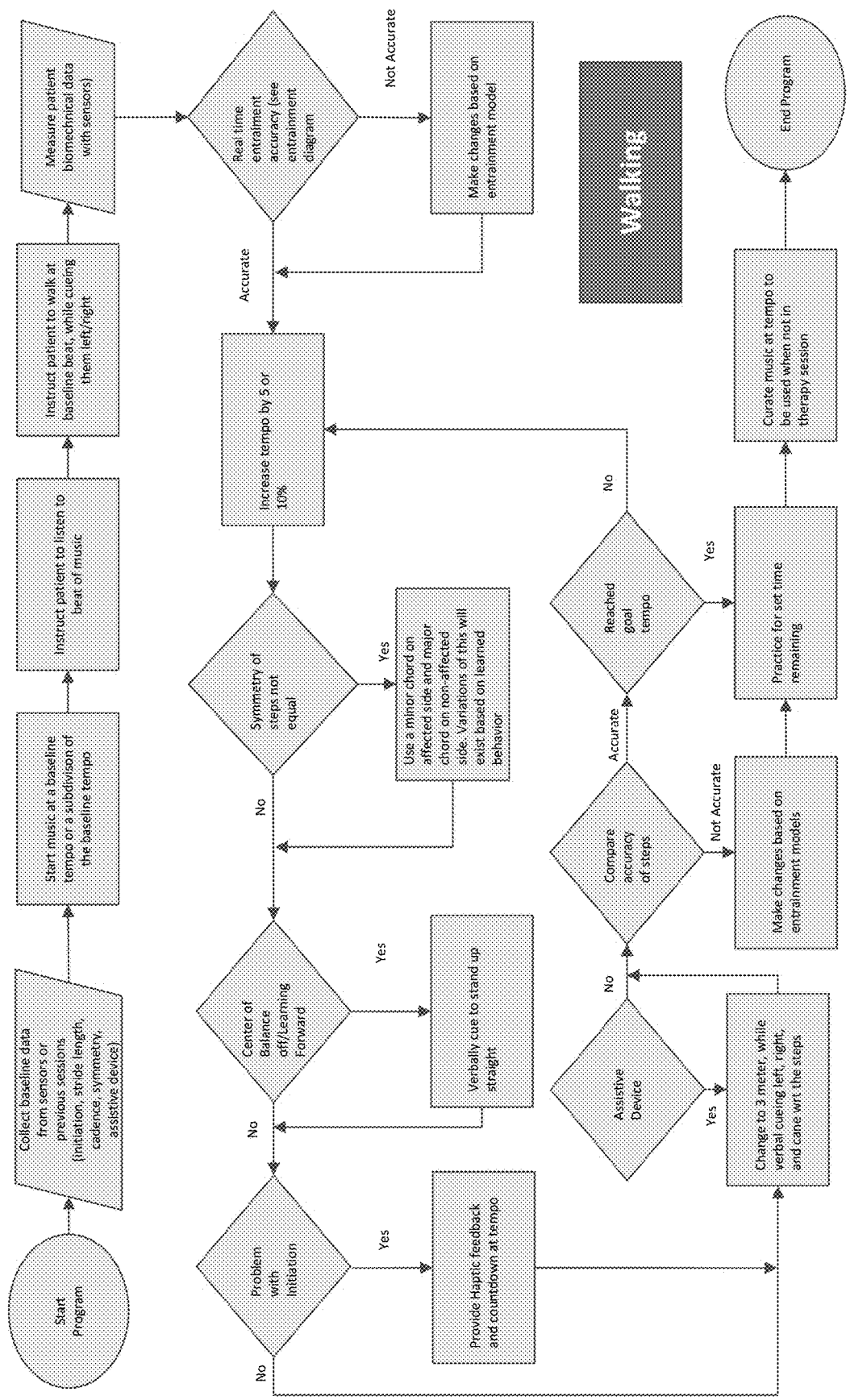
FIGS. 18-23 are exemplary embodiments of various therapeutic movements in accordance with the present disclosure.
Figure 19:
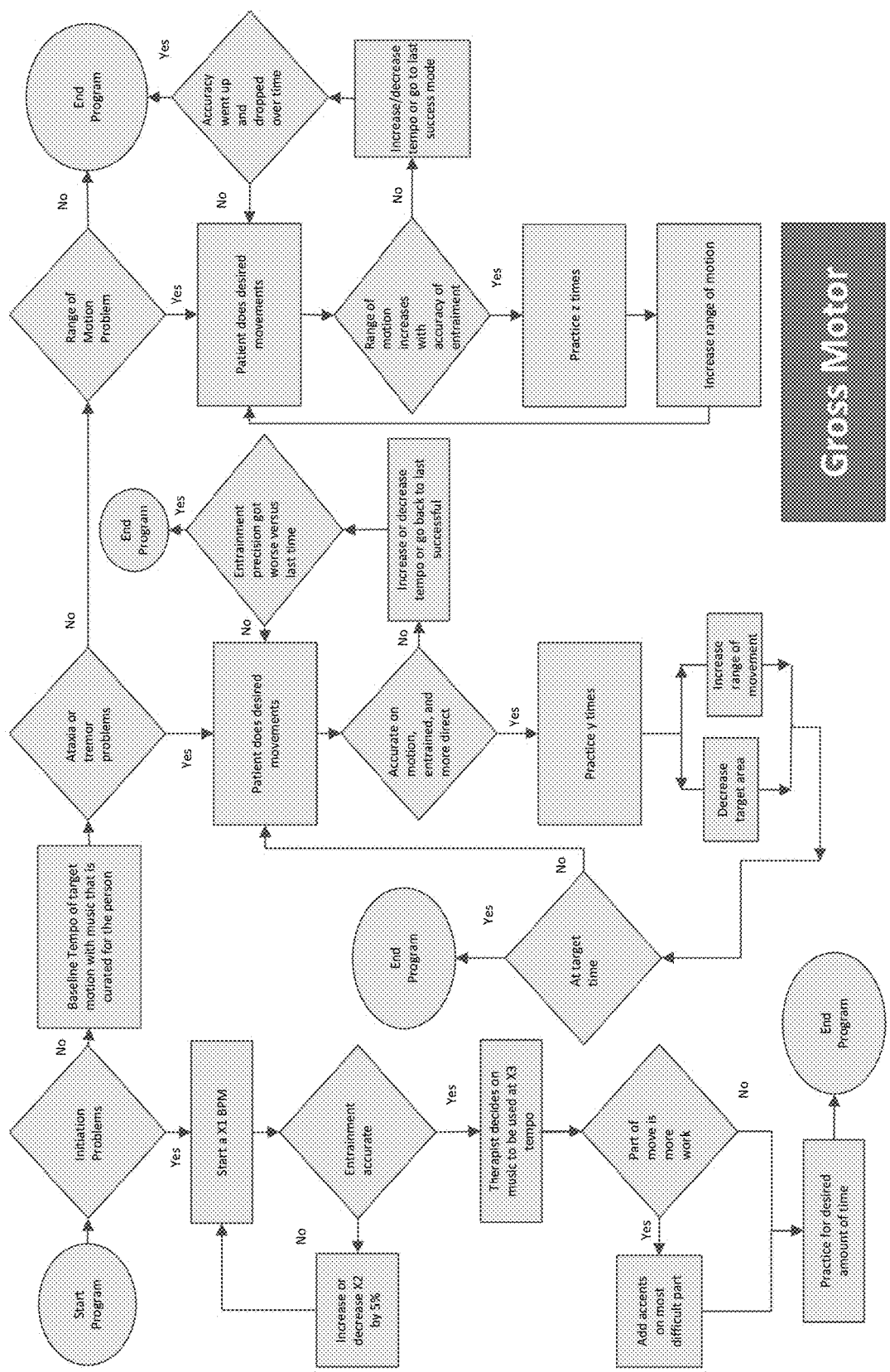
Figure 20A:
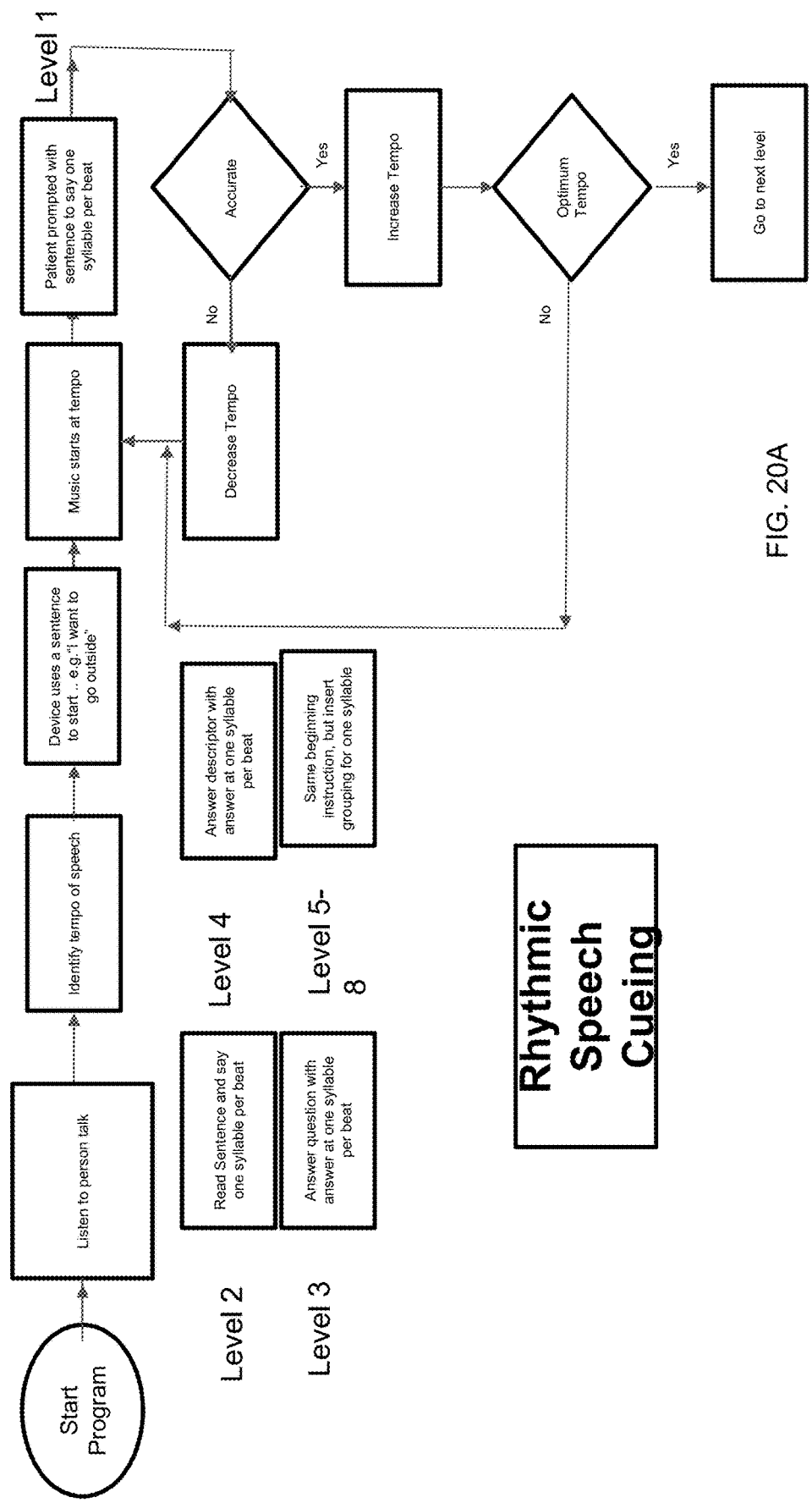
Figure 20B:
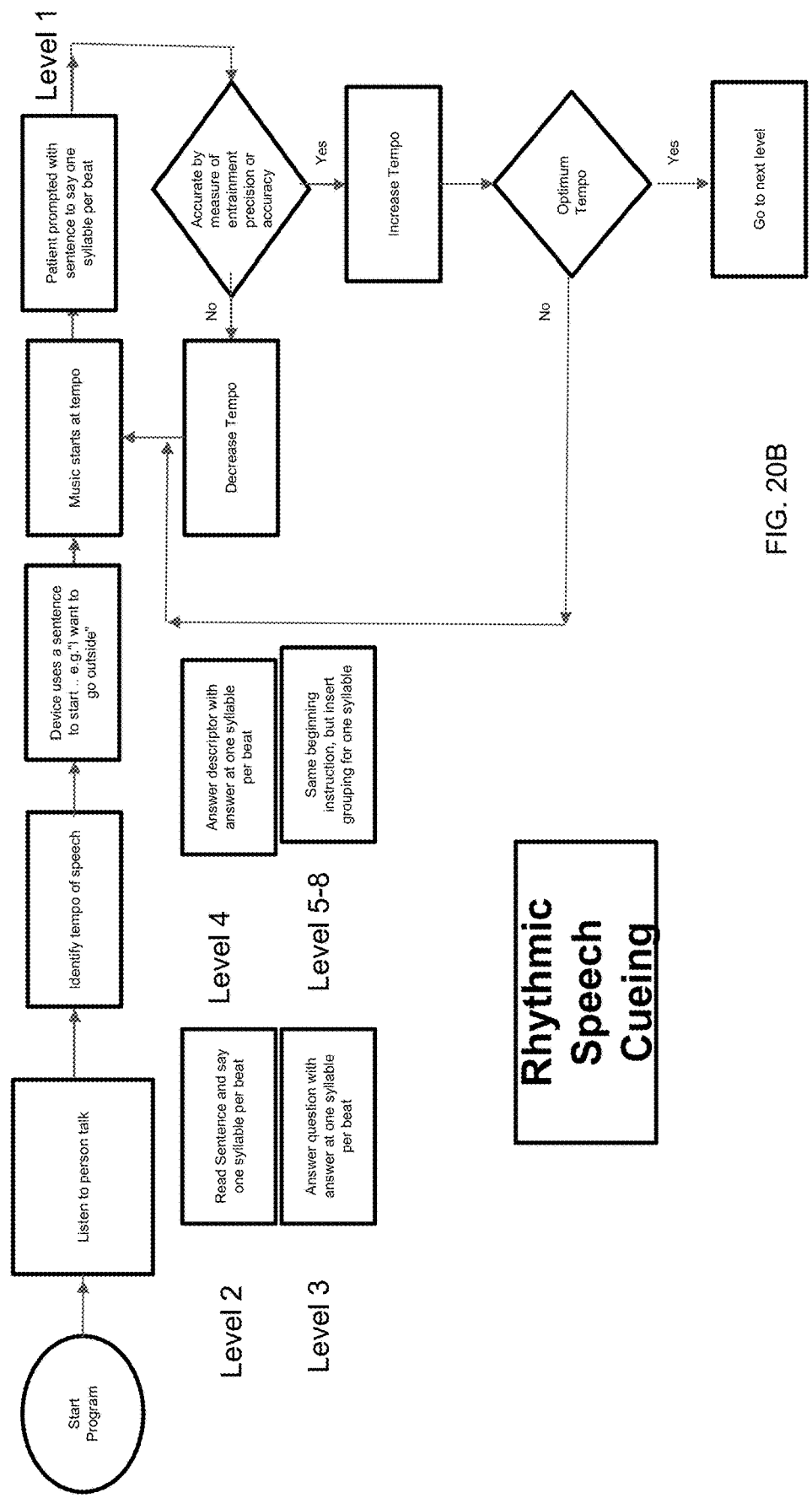
Figure 21:
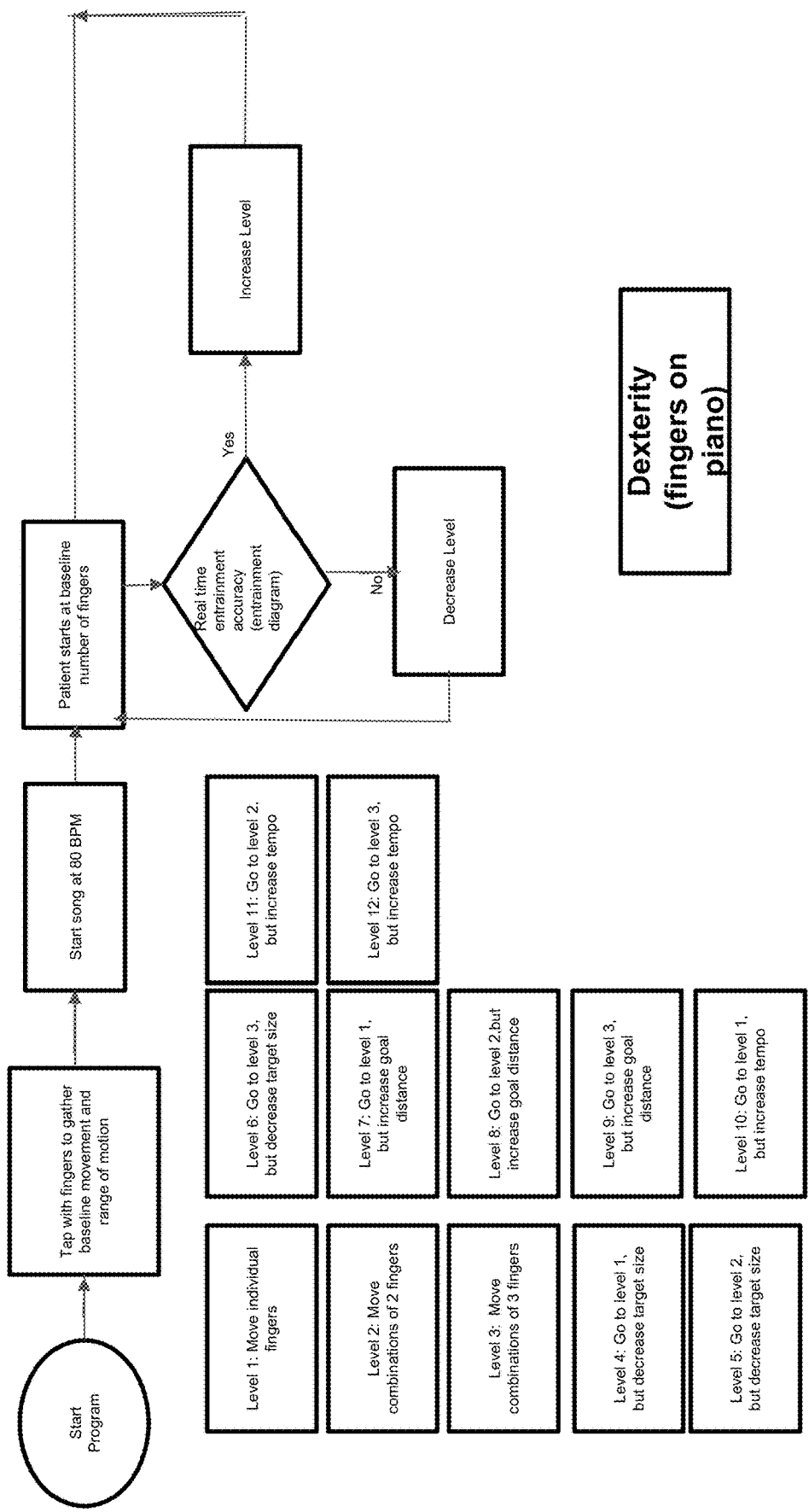
Figure 22:
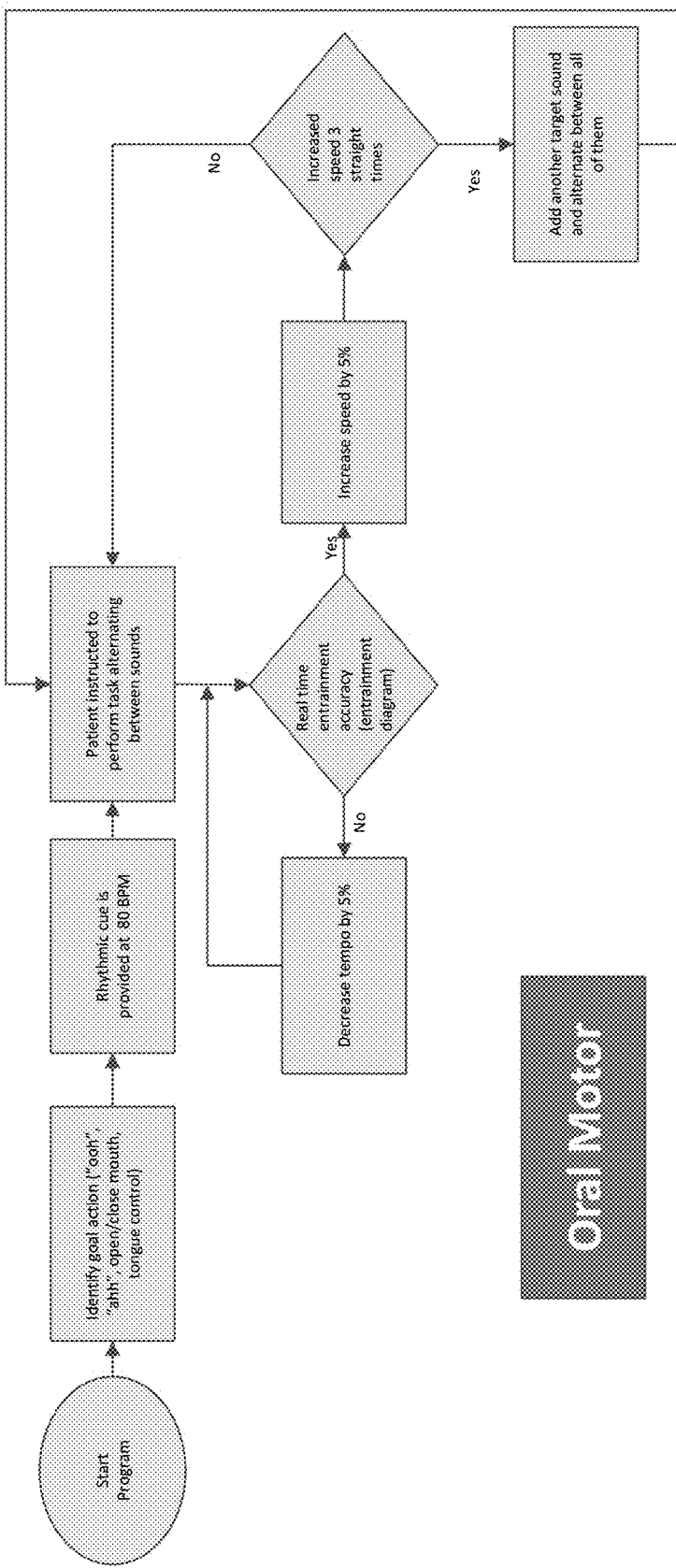
Figure 22:
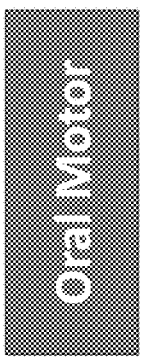
Figure 23:
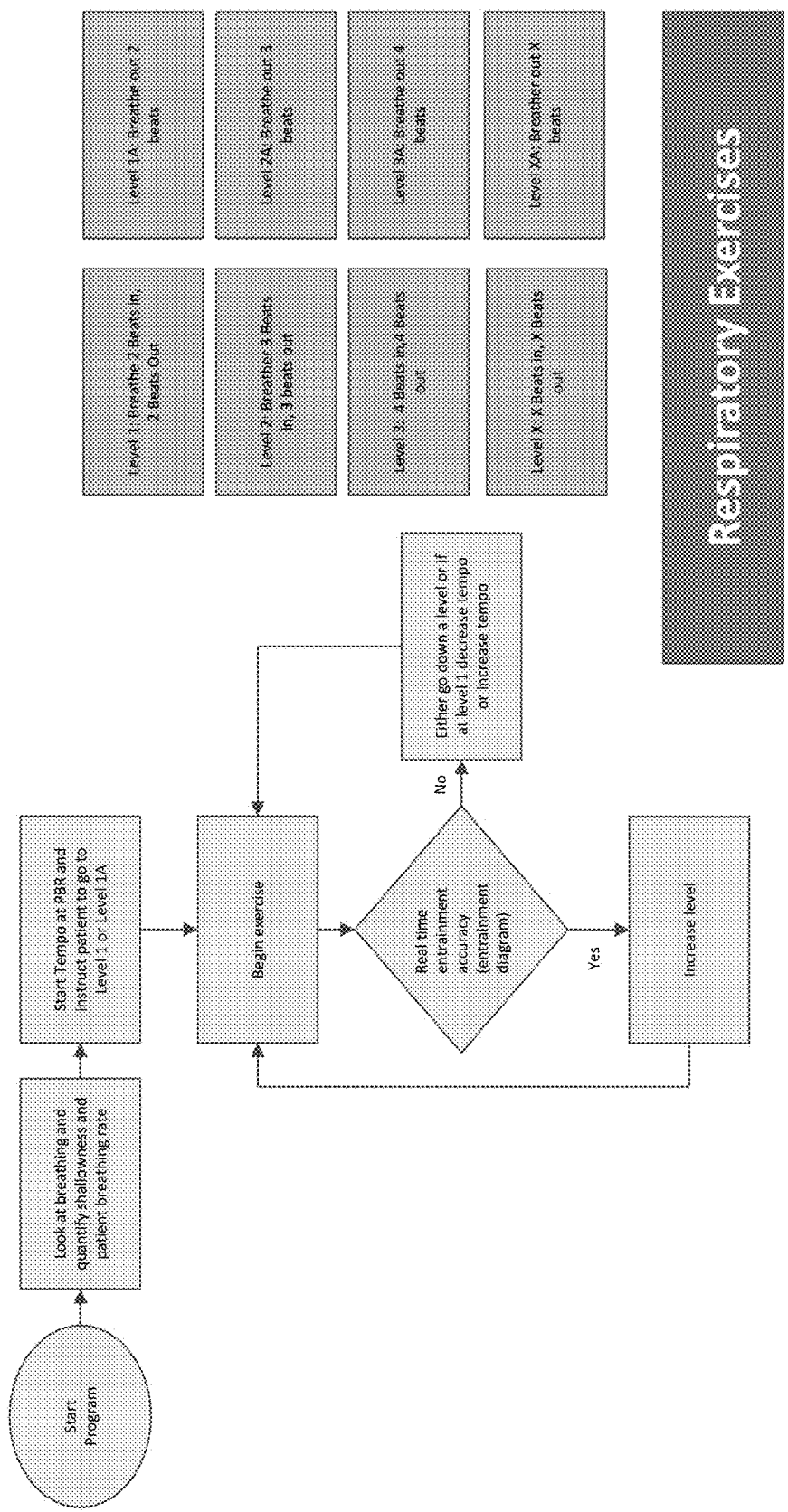

The decision-making system utilized in entrainment sessions is based on FIGS. 5-10 below represent many different kinds of repetitive motion activities that this could apply, but it is not limited to these. The activities diagramed are walking (FIG. 18), gross motor movements (FIG. 19), rhythmic speaking (FIG. 20), dexterity/fine motor movements (FIG. 21), oral motor (FIG. 22), and respiratory exercise (FIG. 23). This includes comparing a patient reaction to the beat of the song.

These flow diagram assumes that to complete an entrainment session it requires sensor components and systems, edge-processing components, collector components, analytics systems, and a music therapy decision making center. These components may be provided on various hardware components. As an example, in one embodiment, the sensor component could be worn on the patient and in another embodiment could be an optical measurement system. The music therapy decision making center could be located on a local or a remote server. All of the components could be located on a singular device.

Entrainment is described as a variable called "entrainment precision", which is a measurement involving the time of the step, as measured by a sensor system, and the time of the beat. This can be distilled into a ratio where the time between two steps is compared to the time between two beats. A value of 1 in the ratio is entrainment with an acceptable band around that number, as demonstrated in FIG. 3, which shows the green dots as entrained steps in a range around 1. This exists because even the most trained musicians cannot be exactly on the beat as calculated by the computer system. This band represents what the human eye perceives as being on beat by watching someone complete a repetitive motion activity. A beat factor, a number used to normalize this entrainment ratio back to 1 for sessions completed at subdivisions or different variations of the beat.

During an entrainment session, another data set can be generated by a person trained in the art of using music for repetitive motion action activities making marks in the data at the times when they believe that a change needs to be made, the entrainment precision is out of bounds, or other items to be noted. This data can be saved with the song to inform future analysis and entrainment assistance cues of this content or similar content.

(5) Learning from Session

Overview

Using data sourced from a sample of entrainment sessions on a particular piece of music, a scoring mechanism can be used to measure a song's entrainability (a person's ability to match cadence and motion with the tempo of a piece of music), which is one measure of such music's effectiveness in a clinical or performance enhancement setting. Further, such data, when convolved with other measured attributes of the music, can be used to create a machine learning algorithm capable of predicting entrainability and therefore clinical effectiveness of untested music.

Result of a Session

One result of an entrainment session (see Section 4—Run Entrainment Session, above) is data about each activity the user performed as well as data on each beat in music. A calculation on a repetitive motion can be used to determine instantaneous cadence for all segments of the activity, and beat data can be used to determine instantaneous tempo for all segments of the music. Convolving these two data sets yields instantaneous entrainment, which is a score of how well the person's movement relates to the music's beat at every point in time during the session. This can be one factor used in scoring a session.

Entrainment Scoring

Discrete metrics are used to score the entrainability of a song as a whole as well as individually defined sections of a song. These metrics may include:

Instantaneous entrainment ("entrainment precision")
Entrainment variance
Number of continuous entrained movements
Lead-in time—amount of time or movements before the user has a high entrainment score
Sampling Strata People of different background or conditions will have different predispositions towards entrainment to different contexts of music. With properly classified data from different groups of people, a machine learning algorithm can be trained to determine entrainability of music for defined categories.

Feedback on Music Augmentation

Given time-sequenced entrainability scores of a particular song before and after musical enhancement have been applied, algorithmic effectiveness can be measured. This effectiveness measurement can provide feedback to the augmentation system, and determine a vector which the augmentation system can use to further augment the music to create a more entrainable song.

Machine Learning System

The machine learning system uses the feature extracted music and compares it to the repetitive motion data, context related data, and measured entrainment scoring data. The presence of these and other data is used to inform the context detection algorithm. For sessions sensor fused data analysis, initially, patient specific Bayesian inference models could be used utilizing Markov chain. The states of the chain represent the specific response patterns captured from the sessions and baseline sessions. The inference is based on knowledge of the response at each sample interval.

The prediction routine, a multi-layer perceptron neural network (MLPNN) uses a directed graph node-based model having a top layer root-node which predicts requirements for reaching a subsequent node and obtaining a person's sensor-fused data feature. The sensor fused data feature vector contains time series processed motion data, music signature data, and other context related data.

The system can use several deep learning neural networks or other machine learning techniques for learning. In one example, a non-linear decision space is built using the adaptive Radial Basis Function (RBF) model generator. New vectors can be calculated using the RBF model and/or with a K-Nearest Neighbor classifier.

One key preparation process for ML model creation is feature engineering. This will include attribute scaling which puts the data to be within a common range which includes zero mean and unit variance. This allows features which can have different physical units like meters, meters/second, meters/second, etc. into a common range of values. Standardization is the process used for scaling the data for zero mean and unit variance. This is done by subtracting from the sampled data value the mean value of all the sampled data, and dividing that by the variance of all the sampled data.

Figure 24:
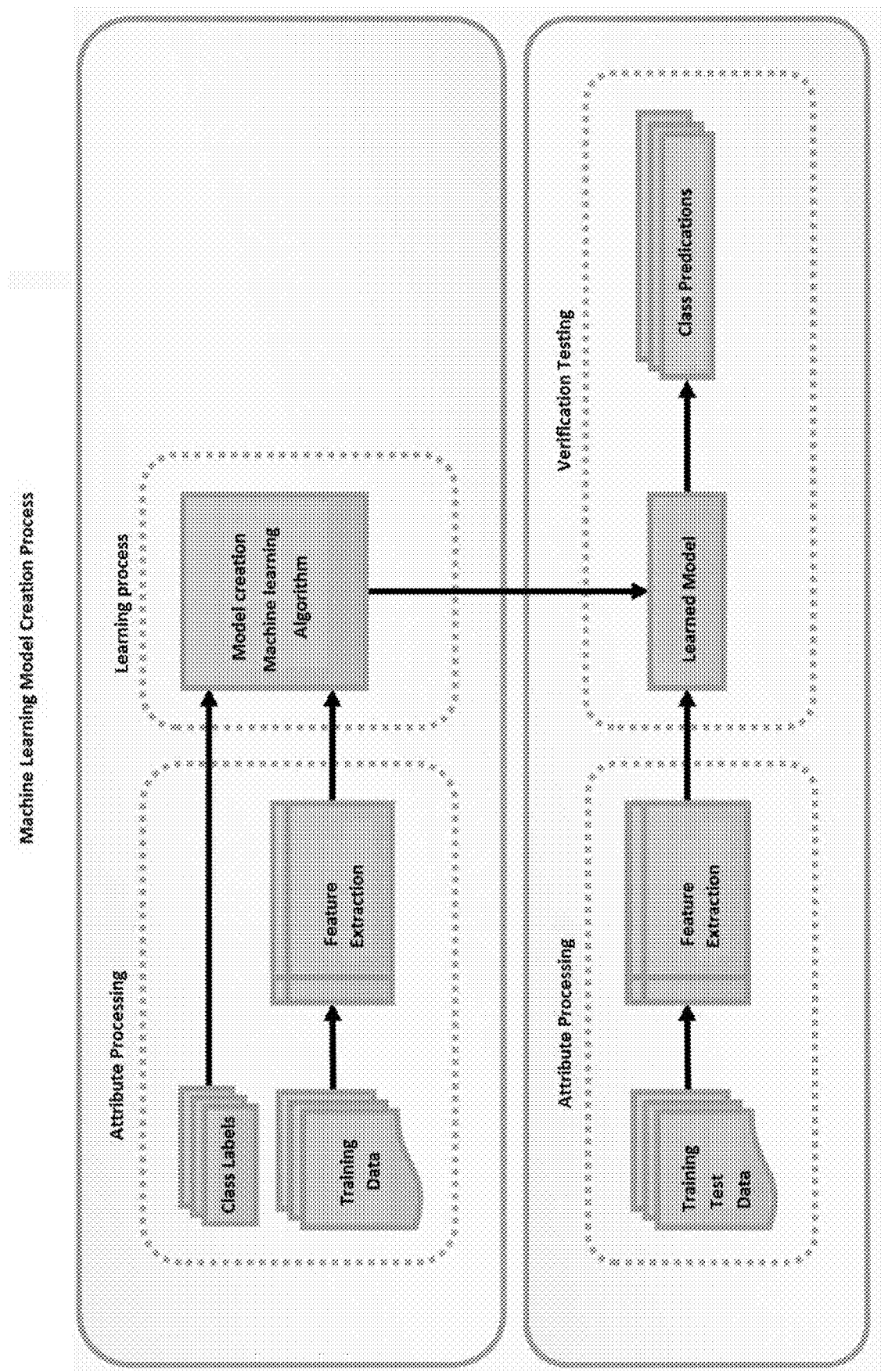
FIG. 24 is a depiction of an exemplary embodiment of machine learning model creation process in accordance with the present disclosure.

In addition, in ML model creation feature engineering process is feature decomposition and aggregation. This is where data is compressed into a smaller number of highly descriptive data components. Aggregation is the process of grouping multiple features into a single salient feature, thus reducing the dimensionality of the data. The model creation process is shown in the exemplary diagram depicted in FIG. 24.

APPENDIX A: BEAT DETECTION WITH DWT (DISCRETE WAVELET TRANSFORMS)

Figure 25:
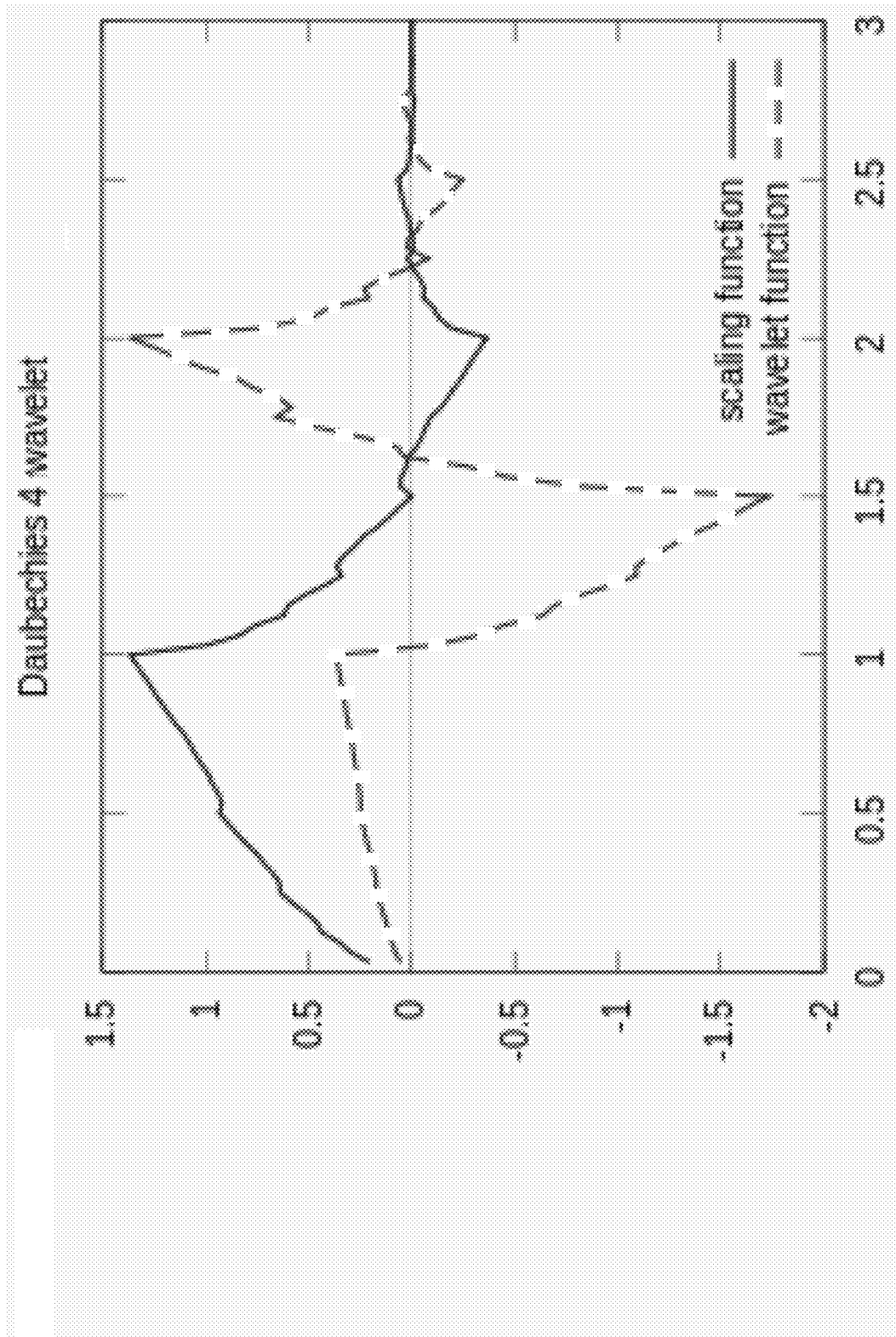
FIGS. 25-34 are depictions of an exemplary embodiments of wavelet transforms in accordance with the present disclosure.

The following analysis demonstrates how discrete wavelet transforms (DWT) are used to determine beat strength and rhythmic stability. This technique can detect onset events, which can be used for beat tracking. This is done by using beat histograms that use the DWT coefficients. The DWT detects the rapid variation of the audio signal from the onset of notes such as on the tempo beats. For the invention, the DWT using the Daubechies db4 wavelet facilitating envelope extraction on each sub-band, and then perform an autocorrelation on the sum of these extracted envelopes. FIG. 25 depicts the Daubechies db4 wavelet.

Figure 26:
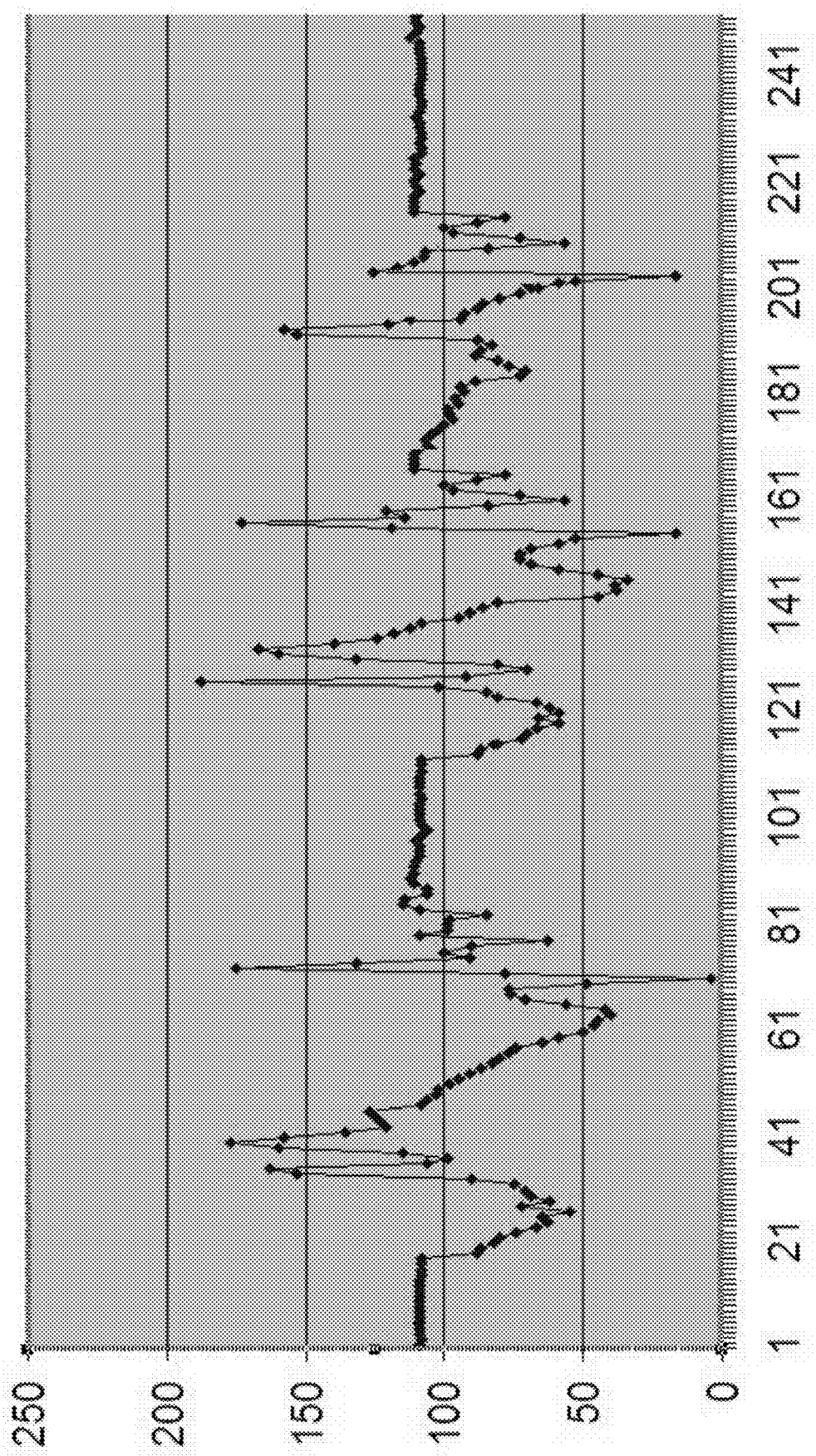

The autocorrelation function allows for maximum peak selection and for histogram creation using the first five peaks of the autocorrelation in the range of 10 to 240 BPM. The envelope extraction from a sub-band x[n] is done using a full wave rectification technique where absolute values are created from the audio signal data which is then low-passed filtered, down-sampled, and the mean removed. FIG. 26 is an example of the beat histogram where the vertical axis is intensity and the horizontal axis is BPM.

FIGS. 27-30 show four examples of separate edge case scenarios that will be analyzed to determine when musical cues should be added.

Figure 27:
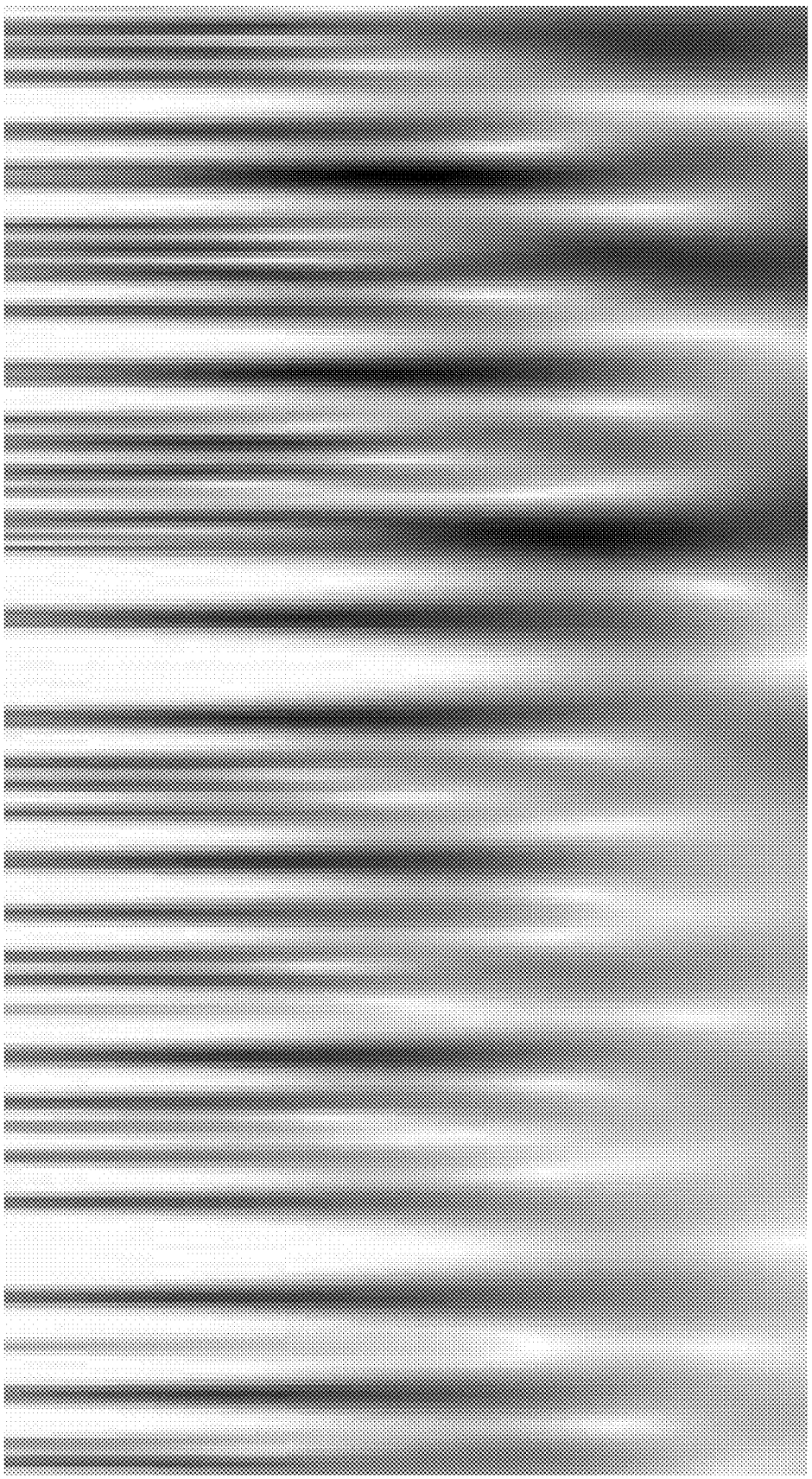

FIG. 27 shows an example of low rhythmic stability because of X-axis irregularity and lack of repetition (non-self-similar). In the DWT image, the X-axis is time, the Y-axis is beat frequency, and the Z-axis is intensity.

Figure 28:
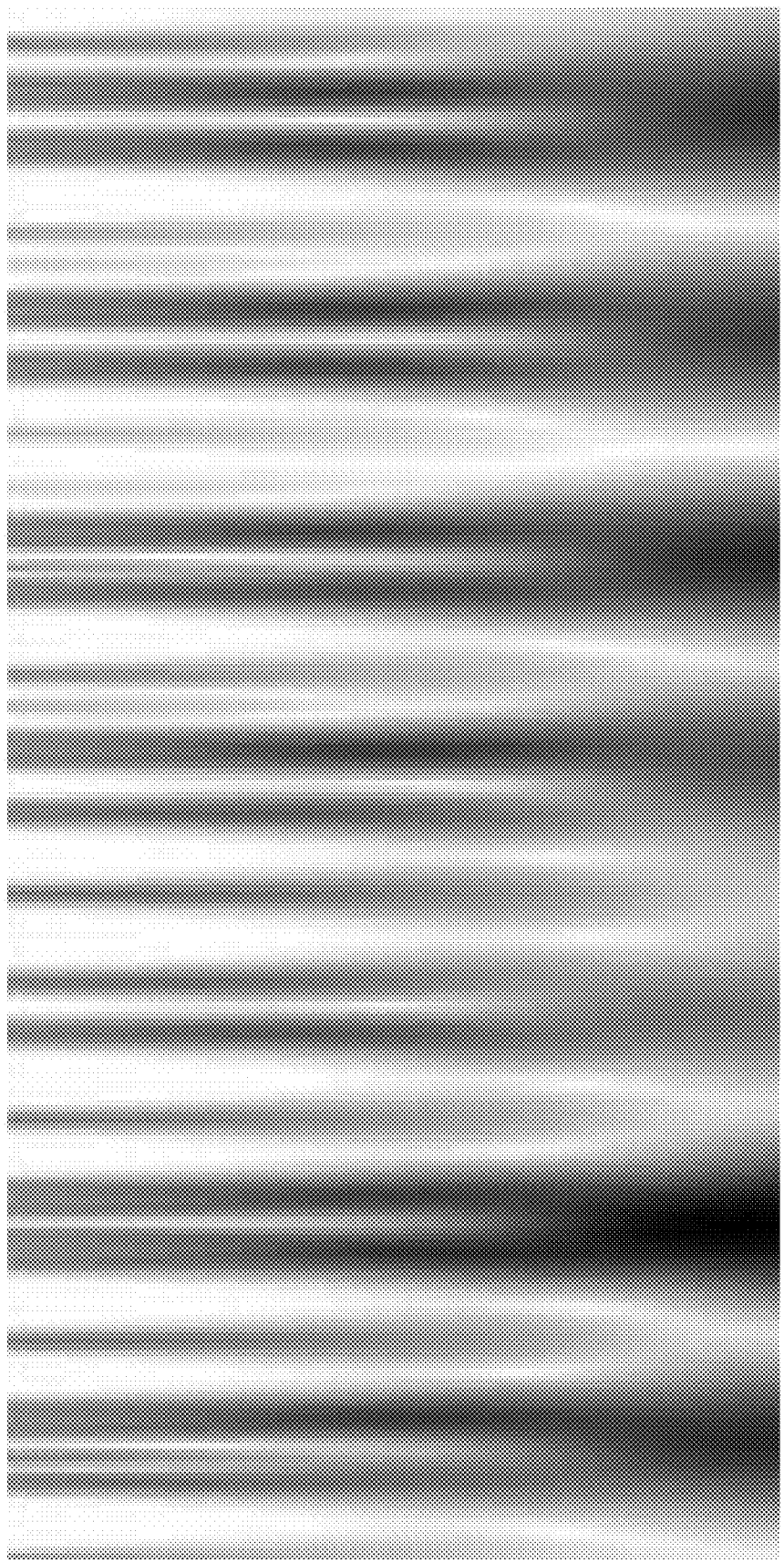
Figure 29:
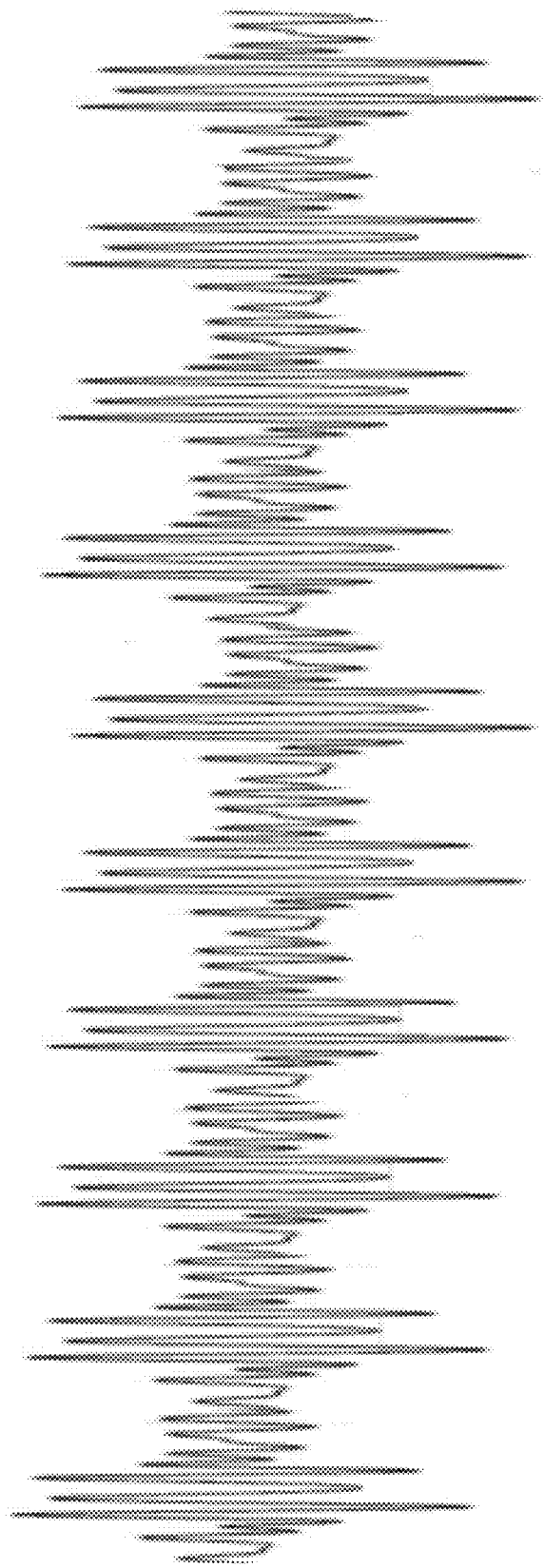

FIG. 28 shows an example of high rhythmic stability. In this DWT image, when viewing the X-axis, one can observe a repetitive (and self-similar) beat pattern. In this DWT display, the X-axis is time, the Y-axis is beat frequency, and the Z-axis is intensity:

FIG. 29 shows an example of low beat strength in amplitude (Y-axis) and time (X-axis).

Figure 30:
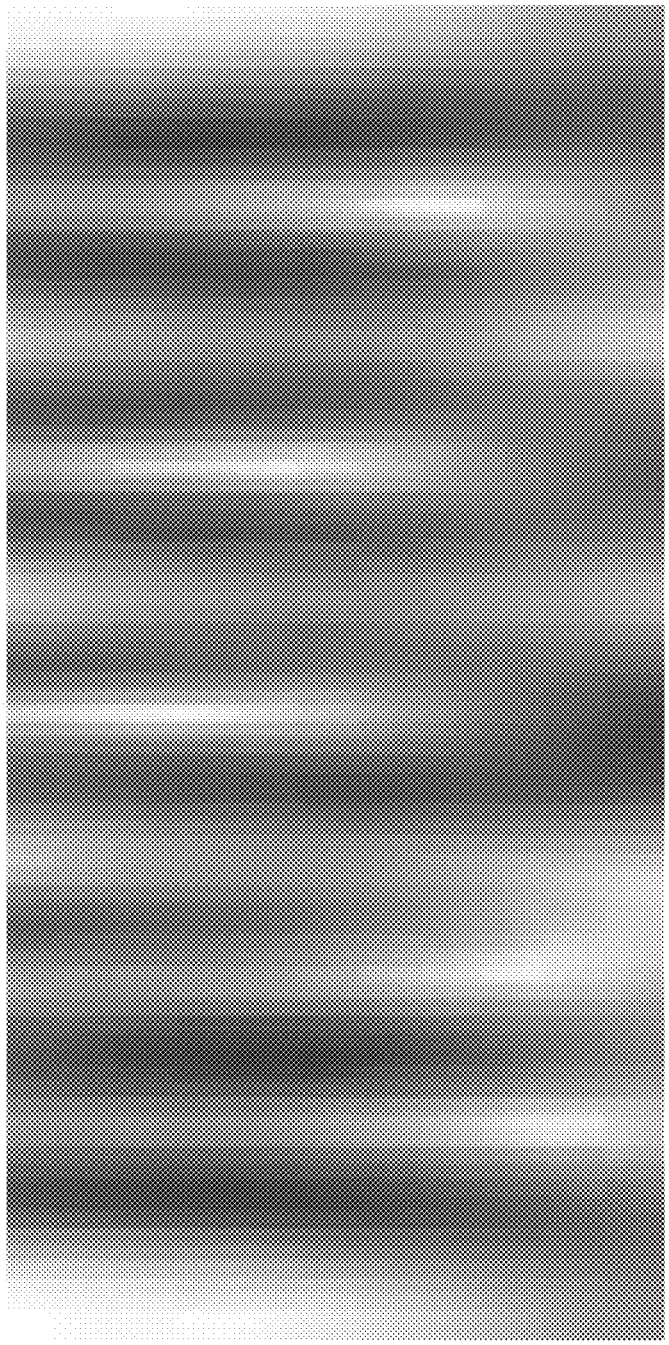

FIG. 30 is a DWT display of the above self-similar low strength beat where the X-axis is time, the Y-axis is beat frequency, and the Z-axis is intensity.

Figure 31:
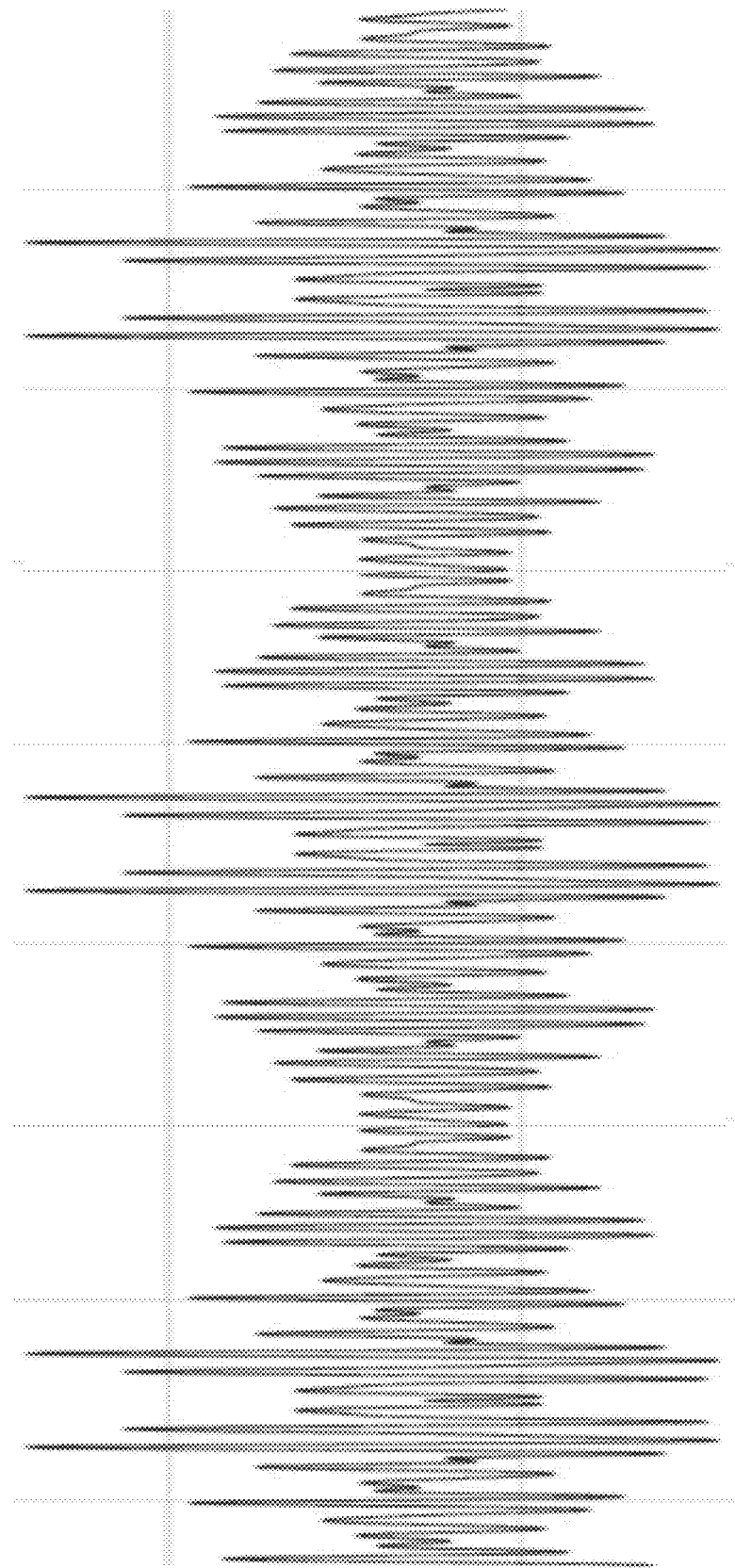

FIG. 31 shows an example of high beat strength in amplitude (Y-axis) and time (X-axis).

Figure 32:
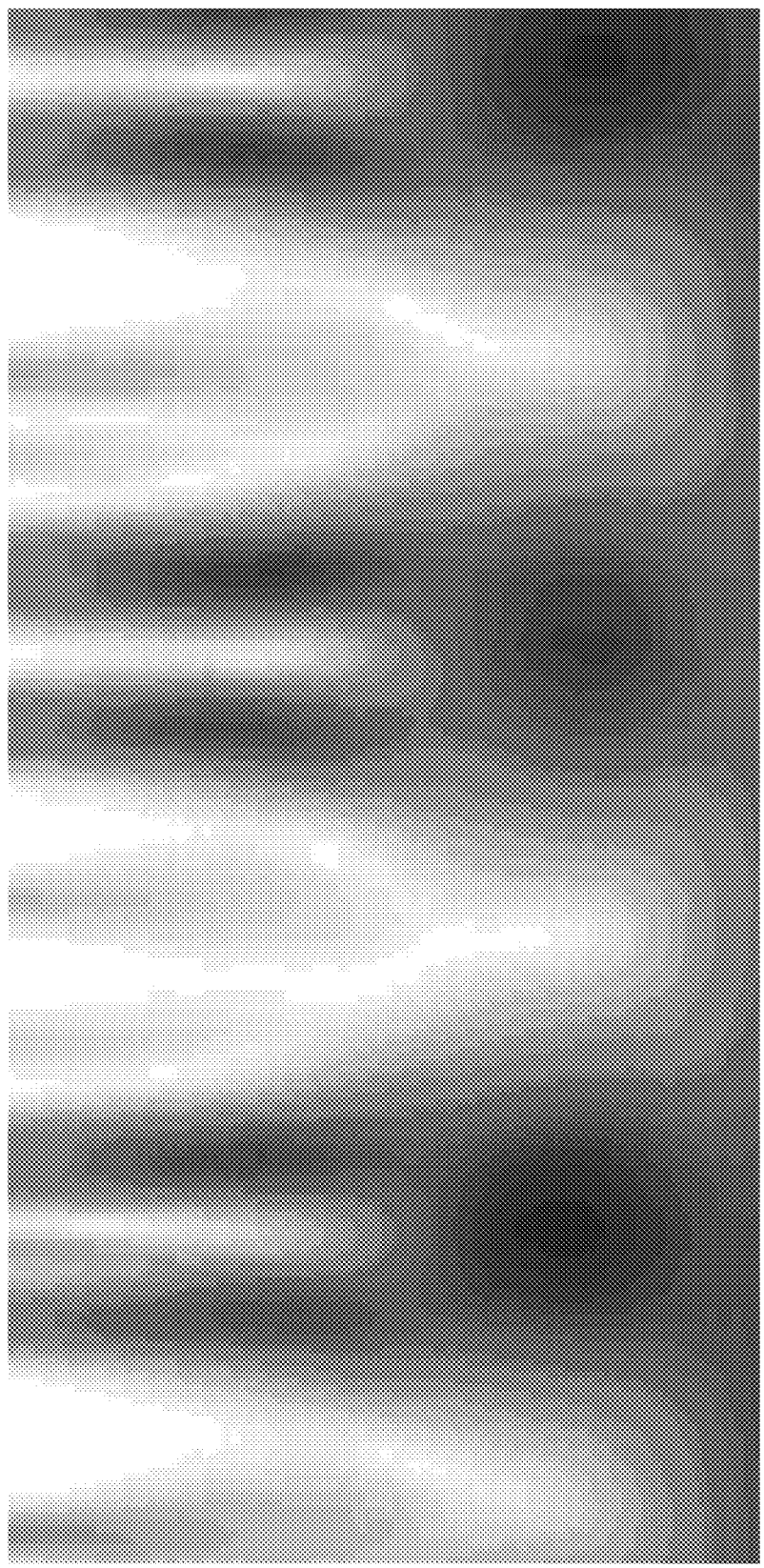

FIG. 32 is a DWT display of the above self-similar high strength beat where the X-axis is time, the Y-axis is beat frequency, and the Z-axis is intensity The frequency range for beat analysis will typically range from 0.25 Hz through 20 Hz. The beat detection algorithm is based on decomposing the signal into a number of octave frequency bands using the DWT. After that, the time domain amplitude modulation envelope of each frequency is extracted separately. This is achieved by low pass filtering each frequency, applying a full wave rectifier function and then down-sampling. The amplitude modulation envelopes of each frequency are then summed together and an auto-correlation function is applied against this data. The peaks of the autocorrelation function correspond to the various periodicities of the signal's envelope.

Figure 33:
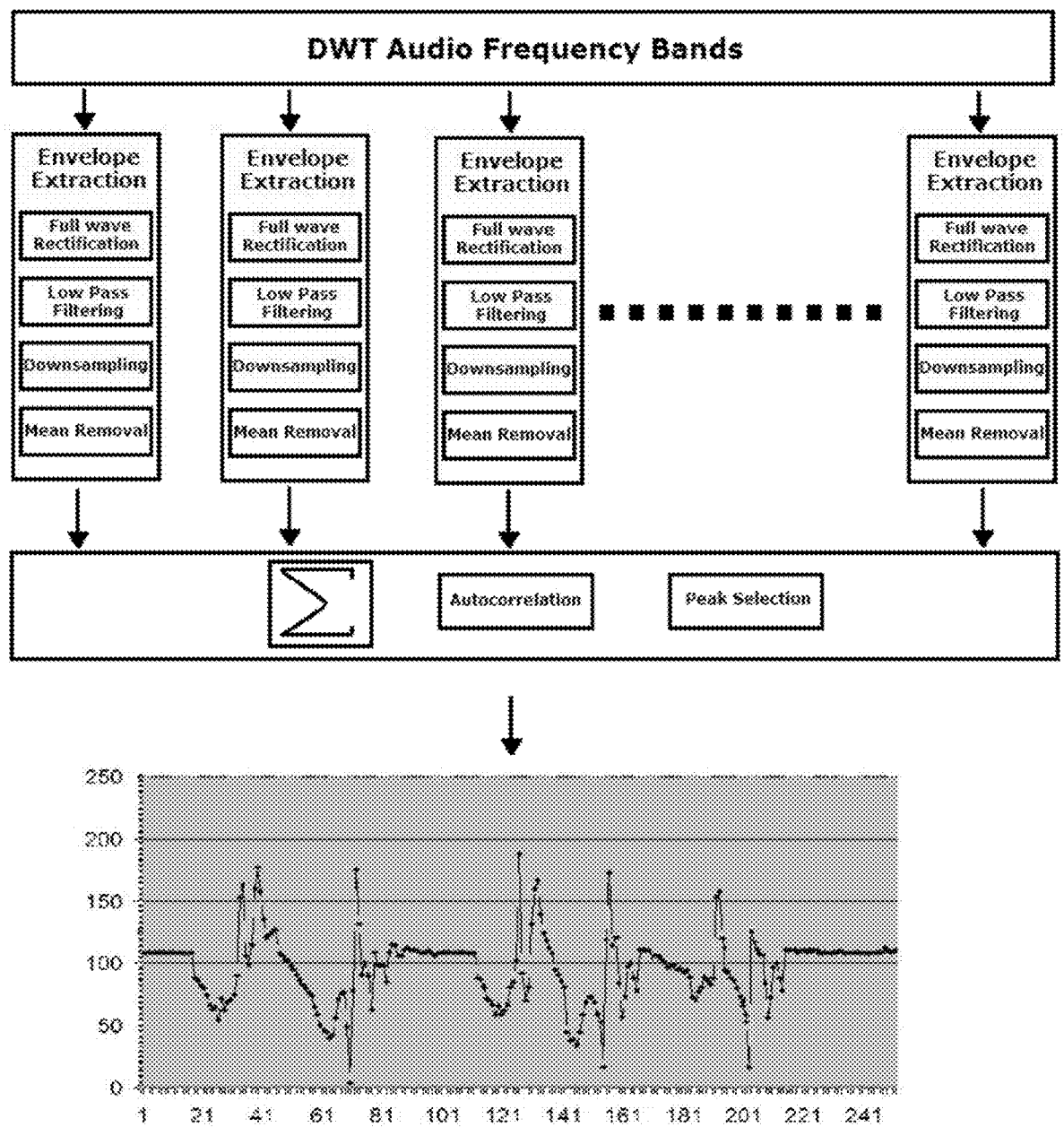

The DWT beat detection and histogram generation process is depicted in FIG. 33.

Onset detection will use some known methods with some additional modification relevant to the invention. It will analyze the audio sample data looking for simultaneous and singularity maxima in the sub-bands to determine for instance, the distance between two consecutive peaks as being the audio signal period. This allows for the detection of the baseline frequency and the next more intense frequency.

Figure 34:
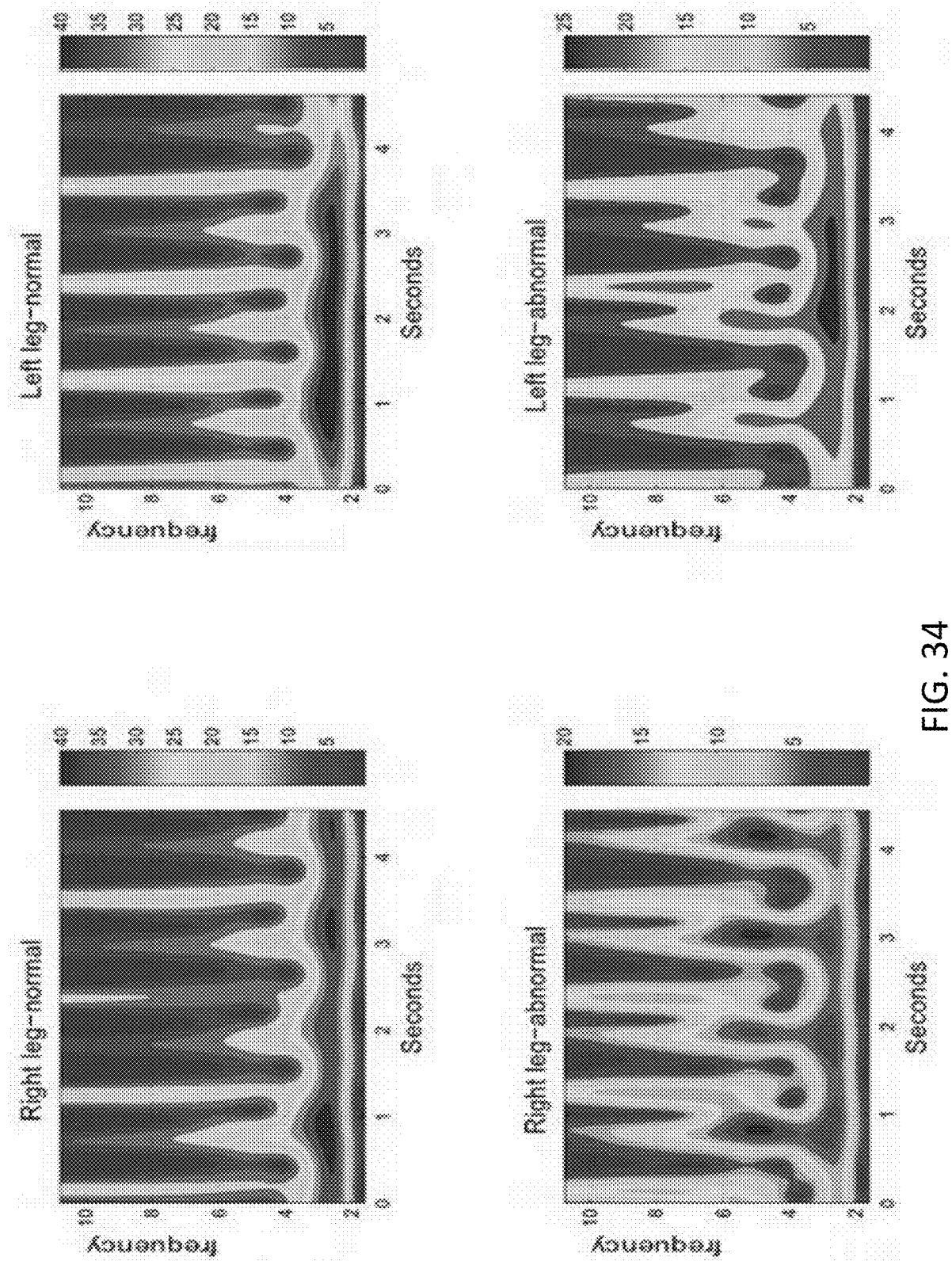

The following information relates to how the DWT can be used for bio-mechanical analysis to then be used in the machine learning engine. This example shows how it is used for the analysis of gait via captured bio-mechanical data, DWT is used to determine time frequency decomposition. The bio-mechanical data is analyzed with DWT with wavelets at different scales by compressing and expanding the Daubechies db4 wavelets and at different times by delaying the Daubechies db4 wavelets. The scale corresponded to the frequency and the position corresponded to the time. The results of the Daubechies db4 DWT are wavelet coefficients. Using the DWT coefficients, a three-dimensional power spectrum is created showing the analysis in time, bio-mechanical frequency and bio-mechanical energy of the bio-mechanical data, shown in FIG. 34.

APPENDIX B: MOTOR, MUSIC, AND THE BRAIN

In human brain anatomy, it is known that the right hemisphere of the brain controls the left side of the body and the left hemisphere controls the right side of the body. Thus, as damage to the left hemisphere occurs, often deficits to the right side of the body are observed and vice versa. Similarly, external auditory cues on either side of the head are processed through the primary auditory cortex of the opposite of the hemisphere of the brain. Thus, we can engage either hemisphere by purposefully placing auditory cues on either side. In cases of movement, we can provide auditory cues through the unaffected side to improve movement of the affected side.

Conversely, using an external auditory cue has also been shown to engage brain regions responsible for attention, including the parietal and temporal lobes. Thus, providing auditory cues through the ear of the affected side, can improved sensory stimulation and attention toward that effective side.

Early studies showed audio-motor pathways in the reticulospinal connections. Priming and timing of movements via these pathways demonstrated the ability of the motor system to couple with the auditory system to drive movement patterns (Rossignol and Melville, 1976). This coupling, through further clinical validation, has been termed "entrainment". Rhythmic entrainment, when clinically applied, has been shown to improve biomechanics of walking, including symmetry, stride length, symmetry, cadence, and gait variability following a neurologic disease or injury, including: stroke, traumatic brain injury, Parkinson's Disease, and Multiple Sclerosis.

The above systems, devices, methods, processes, and the like may be realized in hardware, software, or any combination of these suitable for an application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in several ways. At the same time, processing may be distributed across devices such as the various systems described above, or all the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless an order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

The invention claimed is:

1. A method of providing repetitive motion therapy, the method being implemented on a computer system having a processor configured by computer-executable code to perform the method, comprising:
    providing, at the processor, access to one or more pieces of audio content;
    selecting, using the processor, a piece of audio content for delivery to a patient;
    performing, by the processor, an analysis on the selected audio content,
        wherein the analysis performed by the processor includes identifying audio features of the selected audio content, and
        extracting, based on the analysis, rhythmic and structural features of the selected audio content;
    performing, by the processor using the extracted rhythmic and structural features, an entrainment suitability analysis on the selected audio content to identify features among the rhythmic and structural features of the selected audio content that are suitable for augmenting using cues to trigger kinematic motion;
    generating, by the processor based on the entrainment suitability analysis, entrainment assistance cues for the selected audio content, the assistance cues including a sound added to one or more of the identified features of the selected audio content;
    applying, by the processor, the assistance cues to the identified features of the selected audio content simultaneously with playing the selected audio content and thereby playing the selected audio content augmented with the assistance cues using an audio output device; and
    evaluating, by the processor based on biomechanical data of the patient captured using a sensor while playing the selected audio content and the assistance cues, a therapeutic effect of the selected audio content and the assistance cues on the patient,
        wherein the selected audio content continues to play when the therapeutic effect meets a therapeutic threshold, and when the therapeutic effect fails to meet the therapeutic threshold repeating one or more of the steps of selecting audio content, performing an entrainment suitability analysis and generating entrainment assistance cues.

2. The method of claim 1, further comprising updating, using the processor, a computer-readable database of audio content to integrate a result from the evaluating step in association with the selected content.

3. The method of claim 1, wherein performing an analysis on the selected audio content includes providing bounds to a beat tracking algorithm.

4. The method of claim 3, wherein the selected audio content includes music and the bounds are an average of tempo of the music genre.

5. The method of claim 1, wherein performing the analysis on the selected audio content includes applying an onset detection function (ODF).

6. The method of claim 5, wherein the ODF transforms a time domain of the audio signal into a time-frequency domain.

7. The method of claim 1, further comprising generating modifications to the selected audio content, with at least one modification including an adjustment to a timing of the selected audio content.

8. The method of claim 1, wherein the selected (audio content is streamed to the patient.

9. A method of providing repetitive motion therapy, the method being implemented on a computer system having a processor configured by computer-executable code to perform the method, comprising:
    providing access to a computer-accessible database containing a plurality of pieces of audio content;
    selecting, using the processor, a piece of audio content for delivery to a patient;
    performing an analysis on the selected audio content,
        wherein the analysis includes identifying audio features of the selected audio content and determining a tempo of the selected audio content;
    evaluating, by the processor based on biomechanical data of the patient captured using a sensor while the selected audio content is played to the patient, a therapeutic effect of the selected audio content on the patient,
        wherein the selected audio content continues to play when the therapeutic effect meets a therapeutic threshold, and when the therapeutic effect does not meet the therapeutic threshold;
    performing, by the processor using the identified audio features, an entrainment suitability analysis on the selected audio content, the entrainment analysis assigning a suitability score to a plurality of music aspects that are suitable for augmenting using cues to trigger kinematic motion;
    generating, by the processor as a function of the suitability score assigned to one or more of the plurality of musical aspects, entrainment assistance cues for the selected audio content, the assistance cues including a sound added to the selected audio content;
    applying, by the processor, the assistance cues to the selected audio content simultaneously with playing the selected audio content and thereby playing the selected audio content augmented with the assistance cues using an audio output device; and updating, by the processor, the database of audio content to integrate a result from the evaluating step.

10. The method of claim 9, wherein the entrainment suitability analysis determines an entrainment suitability score for at least one of the following: average tempo, beat strength, beat times confidence, rhythmic stability, time signature, tempo perception confidence, or effective duration.

11. The method of claim 9, wherein generating entrainment assistance cues includes a single beat musical cue which is played on each beat of the selected audio content.

12. The method of claim 9, wherein the musical cues are delivered to a single ear of the patient.

13. The method of claim 9, wherein the musical cues are added to sections of the selected audio content exhibiting low rhythmic stability.

14. The method of claim 9, further comprising generating modifications to the selected audio content, with at least one modification including an adjustment to a timing of the selected audio content.

15. The method of claim 14, wherein generating modifications to the selected audio content includes providing drum reinforcement to the selected audio content.

16. The method of claim 14, wherein generating modifications to the selected audio content includes providing structural modification to the selected audio content.

17. The method of claim 14, wherein generating modifications to the selected audio content includes stretching the selected audio content to change the tempo.

18. A method of providing repetitive motion therapy, the method being implemented on a computer system having a processor configured by computer-executable code to perform the method, comprising:

providing, at the processor, access to one or more pieces of audio content;

selecting, using the processor, a piece of audio content for delivery to a patient;

performing, by the processor, an analysis on the selected audio content, wherein the analysis includes identifying audio features of the selected audio content and determining a tempo of the selected audio content;

performing, by the processor, an entrainment suitability analysis on the selected audio content, wherein the entrainment suitability analysis includes assigning a suitability score to aspects of the selected audio content including at least one of:

average tempo, beat strength, tempo variance, tempo perception, time signature, rhythmic pattern variance, song duration;

detection of rhythmic parts at a plurality of sections throughout the audio content, and position of first and last beat in the selected audio content;

generating, by the processor as a function of the suitability score assigned to the aspects of the selected audio content, entrainment assistance cues to the audio content, the assistance cues including a sound added to the selected audio content, the sound added including at least one of:

a single percussive sound, played on a beat of the selected audio content;

a percussive sound, played on a beat of the selected audio content and its subdivisions;

a drum pattern synchronized with the selected audio content; and a voice counting beats of the selected audio content; and providing the repetitive motion therapy to the patient by playing, using an audio output device, the selected audio content and the assistance cues to the patient.

19. The method of claim 18, further comprising assigning an entrainability score to the selected audio content based on a correlation of the patient cadence with the tempo of the selected audio content.

20. The method of claim 18, wherein the entrainability score is determined before and after application of the entrainment assistance cues to the selected audio content.

* * * * *